United States Patent
Dunn et al.

(10) Patent No.: US 8,293,778 B2
(45) Date of Patent: Oct. 23, 2012

(54) HETEROCYCLIC ANTIVIRAL COMPOUNDS

(75) Inventors: James Patrick Dunn, Los Altos, CA (US); Todd Richard Elworthy, Los Gatos, CA (US); Dimitrios Stefanidis, Mountain View, CA (US); Zachary Kevin Sweeney, Redwood City, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 351 days.

(21) Appl. No.: 12/709,473

(22) Filed: Feb. 20, 2010

(65) Prior Publication Data

US 2011/0207688 A1 Aug. 25, 2011

Related U.S. Application Data

(62) Division of application No. 11/190,478, filed on Jul. 27, 2005, now Pat. No. 7,666,891.

(60) Provisional application No. 60/591,311, filed on Jul. 27, 2004.

(51) Int. Cl.
| | | |
|---|---|---|
| A61K 31/44 | (2006.01) | |
| A61K 31/427 | (2006.01) | |
| A61K 31/4725 | (2006.01) | |
| A61K 31/496 | (2006.01) | |
| A61K 31/513 | (2006.01) | |
| A61K 31/536 | (2006.01) | |
| A61K 31/7068 | (2006.01) | |
| A61K 31/7072 | (2006.01) | |
| A61K 31/708 | (2006.01) | |

(52) U.S. Cl. ............ 514/384; 514/45; 514/50; 514/274; 514/49; 514/230.5; 514/220; 514/307; 514/365; 514/253.09

(58) Field of Classification Search .................... 514/44, 514/45, 384, 220, 230.5, 253.09, 274, 307, 514/365, 49, 50
See application file for complete search history.

(56) References Cited

U.S. PATENT DOCUMENTS

| | | |
|---|---|---|
| 3,274,185 A | 9/1966 | Sigal, Jr. et al. |
| 3,813,384 A | 5/1974 | Vogelsang et al. |
| 4,826,990 A | 5/1989 | Musser et al. |
| 4,942,236 A | 7/1990 | Musser et al. |
| 5,103,014 A | 4/1992 | Musser et al. |
| 5,331,002 A | 7/1994 | Miller |
| 5,436,252 A | 7/1995 | Sorensen et al. |
| 6,248,769 B1 | 6/2001 | Cavalla et al. |

FOREIGN PATENT DOCUMENTS

| | | |
|---|---|---|
| EP | 0 273 309 B1 | 1/1995 |
| EP | 0 273 310 B1 | 6/1995 |
| WO | WO 97/40017 A2 | 10/1997 |
| WO | WO 98/04135 | 2/1998 |
| WO | WO 00/03998 A1 | 1/2000 |
| WO | WO 02/38553 | 5/2002 |
| WO | WO 02/40021 A2 | 5/2002 |
| WO | WO 02/40021 A3 | 5/2002 |
| WO | WO 2004/085411 A1 | 10/2004 |

OTHER PUBLICATIONS

Buckheit, Jr., Robert W., Non-nucleoside reverse transcriptase inhibitors: perspectives on novel therapeutic compounds and strategies for the treatment of HIV infection, *Expert Opinion*, Investigative Drugs, Ashley Publications, Ltd., 2001, pp. 1423-1442, vol. 10, No. 8.

Bundgaard, H., *Design of Prodrugs: Bioreversible derivatives for various functional groups and chemical entities in Design of Prodrugs*, H. Bundgaard (ed) Elsevier Science Publishers, Amersterdam 1985, pp. 10-27.

De Clercq, Erik, "New Developments in Anti-HIV Chemotherapy," *Current Medicinal Chemistry*, 2001, pp. 1543-1572, vol. 8, No. 13, Bentham Science Publishers Ltd.

Del Olmo, Esther, et al., "Anti-Trypanosoma Activity of Some Natural Stilbenoids and Synthetic Related Heterocyclic Compounds", *Bioorganic & Medicinal Chemistry Letters*, 2001, pp. 2755-2757, No. 11.

Del Olmo, Esther, et al., "Leishmanicidal Activity of Some Stilbenoids and Related Heterocyclic Compounds," *Bioorganic & Medicinal Chemistry Letters*, 2001, pp. 2123-2126, No. 11.

Ettmayer, P., et al., "Lessons Learned from Marketed and Investigational Prodrugs", *J. Med. Chem.* 2004 47(10): 2393-2404.

Rosen, Gerald M., et al., "2-Benzyl-1,3,4-oxadiazolin-5-one and Related Compounds," *Notes*, Dept. of Chemistry, Clarkson College of Technology, Potsdam, NY, Aug. 1971, pp. 659-662.

Varia, S. A., "Phenytoin Prodrugs III: Water soluble prodrugs for Oral and/or Parental Use," *J. Pharm. Sci.*, 1984 73(8):1068-1073.

*Primary Examiner* — Jennifer M Kim

(74) *Attorney, Agent, or Firm* — Brian L. Buckwalter

(57) ABSTRACT

The present invention relates to a method of treating an HIV-I infection with a compound according to formula I where $R^1$, $R^2$, $R^3$, $R^4$, $R^5$, are as defined herein.

(I)

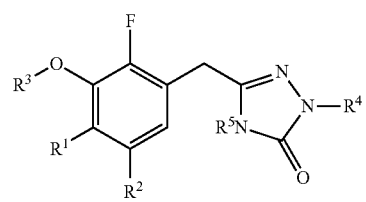

6 Claims, No Drawings

HETEROCYCLIC ANTIVIRAL COMPOUNDS

CROSS REFERENCE TO RELATED APPLICATIONS

This application is a divisional application of Ser. No. 11/190,478, now U.S. Pat. No. 7,666,891, filed Jul. 27, 2005 which claims the benefit of priority to U.S. Ser. No. 60/591,311 filed Jul. 27, 2004 both of which are hereby incorporated by reference in its entirety.

FIELD OF THE INVENTION

The invention relates to the field of antiviral therapy and, in particular, to non-nucleoside reverse transcriptase inhibitors for treating Human Immunodeficiency Virus (HIV) mediated diseases including AIDS and ARC (AIDS Related Complex). The invention provides novel triazolone compounds, pharmaceutical compositions comprising these compounds, methods for treatment or prophylaxis of HIV mediated diseases employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the CD4+ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al. *Antiretroviral therapy: 'the state of the art"*, Biomed & Pharmacother. 1999 53:63-72; R. W. Shafer and D. A. Vuitton, *Highly active retroviral therapy (HAART) for the treatment of infection with human immunodeficiency virus type I*, Biomed. & Pharmacother. 1999 53:73-86; E. De Clercq, *New Developments in Anti-HIV Chemotherap. Curr. Med. Chem.* 2001 8:1543-1572) Two general classes of RTI inhibitors have been identified: nucleoside reverse transcriptase inhibitors (NRTI) and non-nucleoside reverse transcriptase inhibitors (NNRTI).

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq *The role of non0-nuceloside reverse transcriptase inhibitors (NNRTIs) in the therapy of HIV-1 infection*, Antiviral Res. 1998 38:153-179; G. Moyle, *The Emerging Roles of Non-Nucleoside Reverse Transcriptase Inhibitors in Antiviral Therapy*, Drugs 2001 61(1):19-26) Although over thirty structural classes of NNRTIs have been identified in the laboratory, only three compounds have been approved for HIV therapy: efavirenz, nevirapine and delavirdine. Although initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT.

While combination therapy with NRTIs, PIs and NNRTIs has, in many cases, dramatically lowered viral loads and slowed disease progression, significant therapeutic problems remain. The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

In WO9804135 published Feb. 5, 1998, J. L. Romain et al. disclose heterocyclic compounds of formula 1 which are potassium channel modulators. Heterocyclic groups disclosed

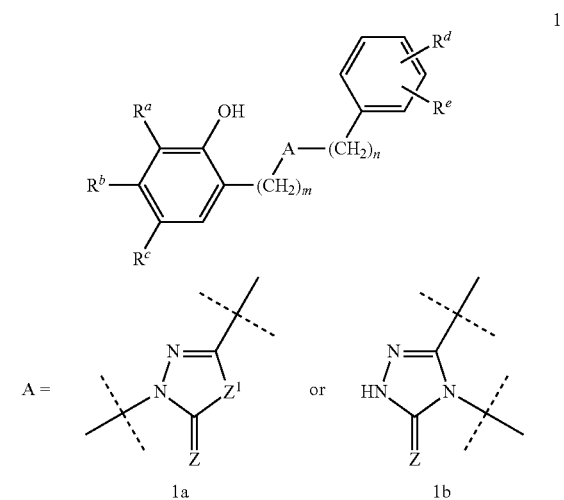

include, inter al., 1a and 1b where Z is O or S, $Z^1$ is O, S or NR and m and n are 0 or 1.

In WO2002038553 published May 16, 2002, M. B. Mantlo et al. disclose triazolone compounds of formula 2 which are peroxisome proliferators Activated Receptor alpha (PPARα) agonists.

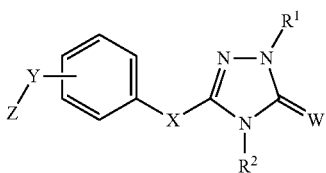

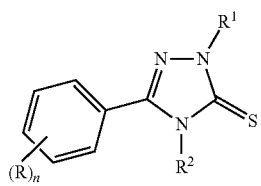

Compounds are disclosed in the invention where X is $(CH_2)_{1-5}$ wherein a carbon atom can optionally be replaced with O, S or NH; $R^1$ and $R^2$ are independently hydrogen, $C_{1-8}$ alkyl, aryl-$C_{0-4}$ alkyl, heteroaryl-$C_{0-4}$ alkyl, $C_{3-6}$ cycloalkyl-$C_{0-2}$ alkyl or $CH_2COR^{17}R^{18}$, Y is O, S, NH, C or a single bond and W is O or S.

In EP 0-435177 published Jul. 3, 1991, John M. Kane and Francis P. Miller disclose triazolones

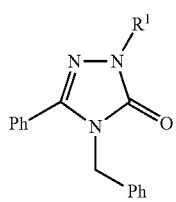

of formula 3 where $R^1$ is hydrogen or $C_{1-4}$ alkyl. Compounds are disclosed to exhibit anticonvulsant activity.

In WO9613264 published May 9, 1996, S. J. Dominianni et al. disclose heterocycles according to

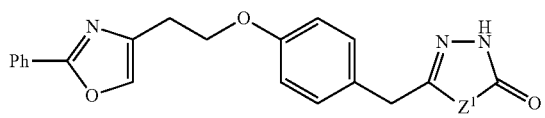

formula 4 and related compounds where $Z^1$ is O, S, or NR exhibit oral hypoglycemic activity.

In U.S. Pat. No. 5,436,252 published Jul. 25, 1995, S. M. Sorenson et al. disclose 5-aryl-3H-1,2,4-triazol-3-ones according to formula 5 wherein $R^1$ is hydrogen or $R^2$, $R^2$ is lower alkyl and R is individually hydrogen, alkyl, alkoxy, hydroxyl, halogen and trifluoromethyl. The disclosed compounds are useful for the treatment of neurodegenerative diseases.

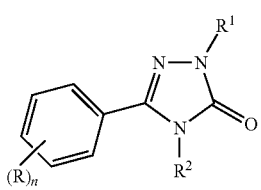

In U.S. Pat. No. 5,331,002 published Jul. 19, 1994, J. A. Miller discloses 5-(optionally substituted)phenyl-4-alkyl-3H-1,2,4-triazole-3-thiones according to formula 105 useful in the enhancement of memory and cognition and treatment of Alzheimer's disease.

H. Yüksek et al. disclose the antibacterial activities of some of triazolones in Synthesis and Antibacterial Activities of some 4,5-Dihydro-1H-1,2,4-triazol-5-ones in Arzneim. Forschung. 1997 47(4):405-409.

Herbicidal and pesticidal properties of triazolones, oxadiazolones and thiadiazolones have been reported. K.-H. Linker et al. disclose pesticidal properties of triazolones in WO 9641535. F. Gozzo et al. disclose insecticidal, nematocidal and acaricidal properties of phosphonic acid esters of triazolones in U.S. Pat. No. 4,400,517 and U.S. Pat. No. 4,220,789. T. Kimata et al. disclose insecticide properties of 1-carbamoyltriazolones in U.S. Pat. No. 5,155,124 and U.S. Pat. No. 5,208,231. K. H. Mueller et al. disclose herbicidal properties of sulfonylaminocarbonyltriazolinones in U.S. Pat. No. 5,532,378 and U.S. Pat. No. 5,625,074. F. Bettarini et al. disclose miticidal and insecticidal activity of (thia)oxadiazol- and triazol(thi)ones in EP 533206. F. Bettarini et al. disclose the synthesis and acaricidal activity of 3-aryl-5-arylmethyl-1,3,4-oxa(thia)diazol-2(3H)-ones in Pesticide Science 1994 40(2):141-6. These compounds are not in the scope of the present disclosure.

U.S. Ser. No. 10/807,766 (U.S. Patent Publication 20040192704) filed Mar. 23, 2004 discloses benzyl-triazolone and benzyl-oxa(thia)diazolone compounds which inhibit HIV reverse transcriptase (HIV RT) U.S. Ser. No. 10/807,993 filed Mar. 23, 2004 (U.S. Patent Publication 20040198736) discloses benzyl-pyridazinone compounds which inhibit HIV RT. A U.S. application filed Apr. 22, 2005 by J. P. Dunn et al. claiming priority to U.S. Ser. No. 60/565,117 filed Apr. 23, 2004 discloses N-aryl 3-phenoxy-phenylacetamide compounds what are inhibitors of HIV reverse transcriptase. These applications are herein incorporated by reference in their entirety. In U.S. Ser. No. 11/085,869 filed Mar. 22, 2005 J. P. Dunn et al. disclose prodrugs of benzyl-pyridazinone compounds, including N-acyloxymethyl derivatives.

Drug failure can result in selection pressure for resistant strains. The facility which mutations occur during HIV replication has resulted in a large number of strains in the infected population. This has resulted in the need for drugs that exhibit activity against a spectrum of reverse transcriptase with one or more point mutations. Since the efficacy generally varies against different mutants, high circulating levels of the active pharmaceutical ingredient must be available to provide adequate activity against even the most resistant strain and avoid selection pressure which would favor resistant strains. The triazolones (I, $R^4$=H) previously disclosed lack sufficient bioavailability to produce adequate blood levels to control all the commonly observed strains.

Chemical derivatization of active drug moieties is frequently undertaken for a variety of reasons including modification of undesirable physical properties of the active drug, optimization of the pharmacokinetic parameters effected absorption, distribution and metabolism of the active ingredient and site-specific targeting or localization of the active moiety to specific target tissues or cells. Albert introduced the term prodrug to describe a compound which lacks intrinsic biological activity but which is capable of in vivo transformation to an active drug substance (A. Albert, Selective Toxicity, Chapman and Hall, London, 1951). While the metabolic transformation can catalyzed by specific enzymes, often hydrolases, the active compound can also be released by non-specific chemical processes. Prodrugs have been recently reviewed (P. Ettmayer et al., J. Med. Chem. 2004 47(10):2393-2404; K. Beaumont et al., Curr. Drug Metab. 2003 4:461-485; H. Bundgaard, Design of Prodrugs: Bioreversible derivatives for various functional groups and chemical entities in Design of Prodrugs, H. Bundgaard (ed) Elsevier Science Publishers, Amsterdam 1985; G. M. Pauletti et al. Adv. Drug Deliv. Rev. 1997 27:235-256; K. Beaumont et al. Curr. Drug Metab. 2003 4:461-485).

Amide (7) prodrugs have included N-hydroxymethyl derivatives (8a) the most common of which are N-acyloxymethyl (8b) compounds. (H. Bundgaard supra, pp 10-27; S. A. Varia et al., J. Pharm. Sci., 1984 73(8):1068-1073).

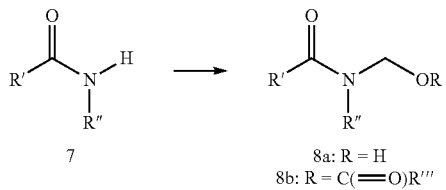

Potential prodrug candidates can sometimes be identified based on the chemical functionality contained in the molecule. However, chemical modifications which alter one aspect of the physical, chemical and biological properties of a molecule may introduce other undesirable properties not observed in the parent molecule. Thus, the identification of prodrugs is an uncertain and challenging exercise.

SUMMARY OF THE INVENTION

The present invention relates to a method for treating an HIV infection, or preventing an HIV infection, or treating AIDS or ARC, comprising administering to a host in need thereof a therapeutically effective amount of a compound according to formula I:

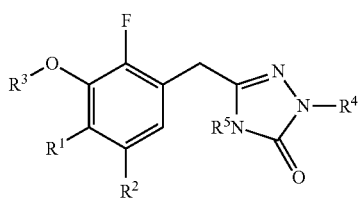

wherein:
$R^1$ is halogen, $C_{1-6}$ alkyl or $C_{1-6}$ alkoxy;
$R^2$ is hydrogen, halogen or $C_{1-6}$ alkyl;
$R^3$ is a phenyl substituted with one to three substituents independently selected from the group consisting of $C_{1-6}$ alkyl, $C_{3-8}$ cycloalkyl, $C_{1-6}$ haloalkyl, $C_{1-6}$ haloalkoxy, halogen, and cyano;
$R^4$ is $CH_2OH$, $CH_2OC(=O)(CH_2)_2C(=O)OH$ or $CH_2C(=O)C_{1-6}$ alkyl;
$R^5$ is hydrogen or $C_{1-6}$ alkyl; and, hydrates, solvates and pharmaceutically acceptable salts thereof.

The present invention also relates to a process for preparing compounds of formula I.

DETAILED DESCRIPTION OF THE INVENTION

The heterocyclic compounds disclosed in U.S. Ser. No. 10/807,766 (U.S. Pat. Application 20040192704) have very limited solubility which complicates formulating the active ingredient. Adequate blood levels of the active ingredient are difficult to attain. Effective administration of anti-HIV compounds requires high doses to control resistant HIV strains. To achieve adequate blood levels of active ingredient in an acceptable dosing regimen requires efficient absorption and distribution of the active ingredient. Surprisingly the modified heterocycles of the present invention show enhanced pharmacokinetic properties.

In one embodiment of the present invention there is provided a compound according to formula I wherein $R^1$, $R^2$, $R^3$, $R^4$ and $R^5$ are as described hereinabove.

In another embodiment of the present invention there is provided a compound according to formula I wherein $R^1$ is methyl, ethyl, bromine and chlorine; $R^2$ is hydrogen; and $R^3$, $R^4$ and $R^5$ are as described hereinabove.

In another embodiment of the present invention there is provided a compound according to formula I wherein $R^1$ is methyl, ethyl, bromine and chlorine; $R^3$ is 3,5-disubstituted phenyl optionally substituted with two groups independently selected from the group consisting of $C_{1-6}$ alkyl, $C_{3-8}$ cycloalkyl, $C_{1-6}$ haloalkyl, $C_{1-6}$ haloalkoxy, halogen, and cyano; and $R^2$, $R^4$ and $R^5$ are as disclosed hereinabove.

In another embodiment of the present invention there is provided a compound selected from the group consisting of: succinic acid mono-{3-[3-(3-cyano-5-difluoromethyl-phenoxy)-4-ethyl-2-fluoro-benzyl]-4-methyl-5-oxo-4,5-dihydro-[1,2,4]triazol-1-ylmethyl}ester; succinic acid mono-{3-[4-bromo-3-(3-cyano-5-difluoromethyl-phenoxy)-2-fluoro-benzyl]-4-methyl-5-oxo-4,5-dihydro-[1,2,4]triazol-1-ylmethyl}ester; succinic acid mono-{3-[3-(3-cyano-5-difluoromethyl-phenoxy)-2-fluoro-4-methyl-benzyl]-4-methyl-5-oxo-4,5-dihydro-[1,2,4]triazol-1-ylmethyl}ester; and, succinic acid mono-{3-[4-chloro-3-(3-cyano-5-difluoromethyl-phenoxy)-2-fluoro-benzyl]-4-methyl-5-oxo-4,5-dihydro-[1,2,4]triazol-1-ylmethyl}ester.

In another embodiment of the present invention there is provided a method for treating an HIV infection, or preventing an HIV infection, or treating AIDS or ARC, comprising administering to a host in need thereof a therapeutically effective amount of a compound according formula I wherein $R^1$, $R^2$, $R^3$, $R^4$ and $R^5$ are as described hereinabove.

In another embodiment of the present invention there is provided a method for treating an HIV infection, or preventing an HIV infection, or treating AIDS or ARC, comprising co-administering to a host in need thereof a therapeutically effective amount of a compound according formula I wherein $R^1$, $R^2$, $R^3$, $R^4$ and $R^5$ are as described hereinabove; and at least one compound selected from the group consisting of HIV protease inhibitors, nucleoside reverse transcriptase inhibitors, non-nucleoside reverse transcriptase inhibitors, CD-4 binding ligands, CCR5 and CXCR4 inhibitors and viral fusion inhibitors.

In another embodiment of the present invention there is provided a method for treating an HIV infection, or preventing an HIV infection, or treating AIDS or ARC, comprising co-administering to a host in need thereof a therapeutically effective amount of a compound according formula I wherein $R^1$, $R^2$, $R^3$, $R^4$ and $R^5$ are as described hereinabove; and at least one compound selected from the group consisting of zidovudine, lamivudine, didanosine, zalcitabine, stavudine, rescriptor, sustiva, viramune, efavirenz, nevirapine and delavirdine, saquinavir, ritonavir, nelfinavir, indinavir, amprenavir and lopinavir; and/or a CD-4/CCR5/CXCR4/viral fusion inhibitor selected T-20, BMS-378806, BMS-488043; Sch-351125, Sch-350634, Sch-417690, UK-4278957, TAK-779, ONO-4128, AK-602, KRH-1636, T-22 or T-134.

In another embodiment of the present invention there is provided a method for inhibiting HIV reverse transcriptase comprising administering a compound according to formula I wherein $R^1$, $R^2$, $R^3$, $R^4$ and $R^5$ are as described hereinabove.

In another embodiment of the present invention there is provided a method for inhibiting an HIV reverse transcriptase with at least one mutation compared to the wild type virus comprising administering a compound according to formula I wherein $R^1$, $R^2$, $R^3$, $R^4$ and $R^5$ are as described hereinabove.

In another embodiment of the present invention there is provided a method for inhibiting an HIV reverse transcriptase expressed by a strain of HIV with reduced susceptibility to efavirenz, nevirapine or delavirdine comprising administering a compound according to formula I wherein $R^1$, $R^2$, $R^3$, $R^4$ and $R^5$ are as described hereinabove.

In another embodiment of the present invention there is provided a method for inhibiting an HIV reverse transcriptase expressed by a strain of HIV with reduced susceptibility to efavirenz, nevirapine or delavirdine comprising co-administering a compound according to formula I wherein $R^1$, $R^2$, $R^3$, $R^4$ and $R^5$ are as described hereinabove; and at least one compound selected from the group consisting of HIV protease inhibitors, nucleoside reverse transcriptase inhibitors, non-nucleoside reverse transcriptase inhibitors, CD-4 binding ligands, CCR5 and CXCR4 inhibitors and viral fusion inhibitors.

In another embodiment of the present invention there is provided a pharmaceutical composition comprising a compound according to formula I wherein $R^1$, $R^2$, $R^3$, $R^4$ and $R^5$ are as described hereinabove in admixture with at least one pharmaceutically acceptable carrier, excipient or diluent in a quantity sufficient upon administration in a single or multiple dose regimen for treating diseases mediated by human immunodeficiency virus inhibit HIV.

In another embodiment of the present invention there is provided a process for the preparation of a compound according to formula I wherein $R^1$, $R^2$, $R^3$, $R^4$ and $R^5$ are as described hereinabove comprising (i) contacting a solution of the heterocycle according to formula I ($R^4$=H) with aqueous formaldehyde and (ii) contacting the resulting N-hydroxymethyl compound of formula I ($R^4$=CH$_2$OH) with an acylating agent.

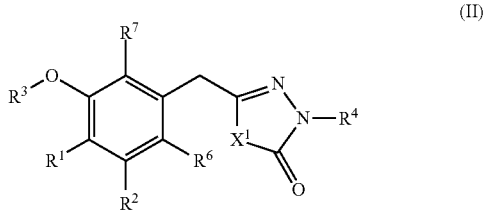

(II)

In another embodiment of the present invention there is provided a compound according to formula II wherein $X^1$ is selected from the group consisting of O, S, and $NR^5$; $R^1$, $R^2$, $R^6$ and $R^7$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, acylamino, nitro and cyano; $R^3$ is an aryl or heteroaryl radical said heteroaryl radical selected from the group consisting of pyridinyl, pyridine N-oxide, pyridine N-oxide, indole, indole N-oxide, quinoline, quinoline N-oxide, pyrimidinyl, pyrazinyl and pyrrolyl; wherein, said aryl and said heteroaryl radicals are optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$N,N-dialkylcarbamoyl, nitro and cyano; $R^4$ is selected from the group consisting of CH$_2$OH, CH$_2$C(=O)X$^2$R$^8$, CH$_2$OCOCH(R$^{12}$)NHR$^{13}$, CH$_2$CO$_2$R$^9$, CH$_2$NR$^{10}$R$^{11}$, CH$_2$OP(=O)(OH)$_2$ and CH(NR$^{10}$R$^{11}$)CO$_2$R$^9$; $R^5$ is hydrogen or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ sulfonyl, halogen, amino, alkylamino, dialkylamino, aminoalkyl, alkylaminoalkyl, and dialkylaminoalkyl; $R^8$ is $C_{1-10}$ alkyl, $C_{1-10}$ heteroalkyl, (CH$_2$)$_n$CO$_2$H, CH=CHCO$_2$H, aryl, (CH$_2$)$_o$NR$^{10a}$R$^{11a}$ and heteroaryl said aryl and said heteroaryl optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$N,N-dialkylcarbamoyl, nitro and cyano; $R^9$ is hydrogen or $C_{1-10}$ alkyl.

In this embodiment $R^{10}$, $R^{10a}$, $R^{11}$ and $R^{11a}$ are independently hydrogen or $C_{1-10}$ alkyl and additionally $R^{10}$ and $R^{11}$ taken together along with the nitrogen atom to which they are attached can form a pyrrolidinyl, piperidinyl, azepinyl, or morpholine ring. Furthermore, $R^{12}$ taken alone is selected from the group consisting of the side chains of naturally occurring amino acids, optionally substituted phenyl and $C_{1-5}$ unbranched or branched alkyl; $R^{13}$ taken alone is selected from the group consisting of hydrogen, or $C_{1-6}$ alkyl; or, $R^{12}$ and $R^{13}$ taken together are (CH$_2$)$_3$. In this embodiment $X^2$ is a bond, O, S, NH; n is 1 to 6; o is 1 to 3. This embodiment further comprises hydrates, solvates, clathrates and acid addition salts of formula II.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition for each group as provided in the Summary of the Invention.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "alkoxy" as used herein means an —O-alkyl group, wherein alkyl is as defined above such as methoxy, ethoxy, n-propoxy, i-propoxy, n-butoxy, i-butoxy, t-butoxy, pentoxy, hexyloxy, including their isomers. "Lower alkoxy" as used herein denotes an alkoxy group with a "lower alkyl" group as previously defined. "$C_{1-10}$ alkoxy" refers to an-O-alkyl wherein alkyl is $C_{1-10}$.

The term "haloalkyl" as used herein denotes an unbranched or branched chain alkyl group as defined above wherein 1, 2, 3 or more hydrogen atoms are substituted by a halogen. "$C_{1-3}$ haloalkyl" as used herein refers to a haloalkyl composed of 1 to 3 carbons and 1-8 halogen substituents. Examples are fluoromethyl, chloromethyl, bromomethyl, iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "haloalkoxy" as used herein refers to a group —OR where R is haloalkyl as defined herein.

The term "halogen" or "halo" as used herein means fluorine, chlorine, bromine, or iodine.

The term "cyano" as used herein refers to a carbon linked to a nitrogen by a triple bond, i.e., —C≡N.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The term "naturally occurring amino acids" as used herein means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Unless specifically indicated, all amino acids referred to in this application are in the L-form. The term "hydrophobic amino acid" as used herein glycine, alanine, valine, leucine, isoleucine, methionine, phenylalanine, tryptophan, and proline. The side chains of naturally occurring amino acids include: hydrogen, methyl, iso-propyl, iso-butyl, sec-butyl, —$CH_2OH$, —$CH(OH)CH_3$, —$CH_2SH$, —$CH_2CH_2SMe$, —$(CH_2)_pCOR$ wherein R is —OH or —$NH_2$ and p is 1 or 2, —$(CH_2)_q$—$NH_2$ where q is 3 or 4, —$(CH_2)_3$—NHC(=NH)$NH_2$, —$CH_2C_6H_5$, —$CH_2$-p-$C_6H_4$—OH, (3-indolinyl)methylene, (4-imidazo lyl)methylene.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddI) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; β-L-FD4 (also called β-L-D4C and named β-L-2',3'-dicleoxy-5-fluoro-cytidene) licensed by Yale University to Vion Pharmaceuticals; DAPD, the purine nucleoside, (−)-β-D-2,6,-diamino-purine dioxo lane disclosed in EP-0656778 and licensed to Triangle Pharmaceuticals; and lodenosine (FddA), 9-(2,3-dideoxy-2-fluoro-β-D-threopentofuranosyl)adenine, an acid stable purine-based reverse transcriptase inhibitor discovered by the NIH and under development by U.S. Bioscience Inc.

The term "non-nucleoside reverse transcriptase inhibitors" ("NNRTI's) as used herein means non-nucleosides that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a furopyridine-thio-pyrimide; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxymethyl)-5-(1-methylethyl)-6-(phenylmethyl)-(2,4(1H,3H)-pyrimidinedione); and (+)-calanolide A (NSC-675451) and B, coumarin derivatives disclosed in U.S. Pat. No. 5,489,697.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as nonpeptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRIXIVAN tradename; nelfnavir (AG-1343) available under the VIRACEPT; amprenavir (141W94), tradename AGENERASE, a non-peptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1549 an orally active imidazole carbamate.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename as a lyophilized powder for IV infusion or sc administration upon reconstitution and dilution with water; a dose of about 1 to about 20 million 1U/day, sc is preferred; a dose of about 15 million 1 U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein. Ribavirin, 1-β-D-ribofuranosyl-1H-1,2,4-triazole-3-carboxamide, is described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. HAART refers to Highly Active Antiretroviral Therapy. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. Clinicians are constantly seeking improved drug regimen and while the exact drugs may differ, HAART refers to the use of multidrug combinations of anti-HIV compounds.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo [3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylamino sulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo [5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diisopropylethylamine (DIPEA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TBDMS),4-N,N-dimethylaminopyridine (DMAP), triethylamine ($Et_3N$ or TEA), N,N-dimethylformamide (DMF), triflate or $CF_3SO_2$— (TO, dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS),4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

COMPOUNDS AND PREPARATION

Examples of representative compounds encompassed by the present invention and within the scope of the invention are provided in Table 1. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

TABLE 1

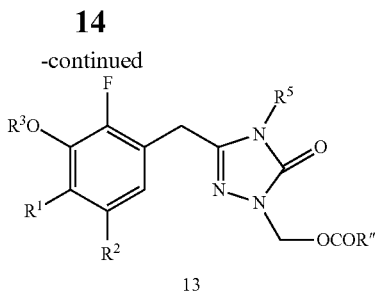

| | $R^1$ | $R^4$ | $R^6$ | MP | MS |
|---|---|---|---|---|---|
| I-1 | Cl | $CH_2OH$ | Cl | 145.8-149.5 | |
| I-2 | Cl | $CH_2OCO(CH_2)_2CO_2H$ | Cl | 136.6-141.9 | |
| I-3 | Cl | $CH_2OH$ | CN | 158.9-162.2 | |
| I-4 | Cl | $CH_2OCO(CH_2)_2CO_2H$ | CN | 141.6-143.3 | |
| I-5 | Cl | $CH_2OCO(CH_2)_2CO_2H$ | $CHF_2$ | 150.5-151.1 | 537 (M – H) |
| I-6 | Cl | $CH_2OH$ | $CHF_2$ | | 440 (M + H) |
| I-7 | Me | $CH_2OCO(CH_2)_2CO_2H$ | $CHF_2$ | 139.2-140.5 | 519 (M + H) |
| I-8 | Me | $CH_2OH$ | $CHF_2$ | | 419 (M + H) |
| I-9 | Br | $CH_2OCO(CH_2)_2CO_2H$ | $CHF_2$ | 156.7-158 | |
| I-10 | Br | $CH_2OH$ | $CHF_2$ | | 483.3 (M + H)+ |
| I-11 | Et | $CH_2OCO(CH_2)_2CO_2H$ | $CHF_2$ | 152.2-153.5 | |
| I-12 | Cl | $CH_2OAc$ | Cl | 72.9-74 | 464 (M – H) |

The compounds of the present invention are prepared from 3-aryloxy-phenylacetic acid compounds 10 by a multi-step process (SCHEME 1) comprising elaborating the triazolone 11, introducing a hydroxymethyl substituent on the nitrogen 12 (X=OH) and acylating the hydroxymethyl adduct 13. $R^1$, $R^2$, $R^3$ and $R^5$ in SCHEME 1 are as defined in claim 1. A variant on this general procedure involves the intermediate conversion of 12 (X=OH) to the corresponding chloromethyl compound 12 (X=Cl) which is subjected to silver(I)-ion assisted nucleophilic displacement with a carboxylic acid. (see Example 6)

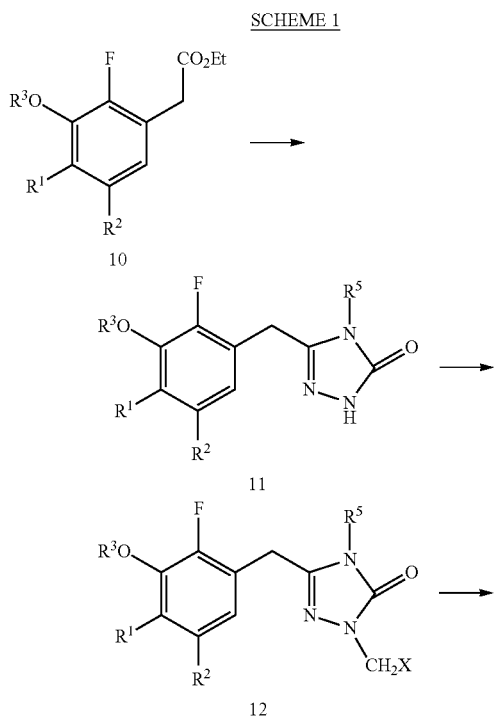

SCHEME 1

Contacting the triazolone compounds II with formaldehyde affords the corresponding hydroxymethyl compound 12 (X=OH). While the adducts are herein depicted as N-hydroxymethyl adducts, a triazolone, in analogy with an amide, is an ambident nucleophile and formaldehyde can, in principle, react with either the nitrogen atom or the adjacent carbonyl oxygen atom. The product ratio derived from ambident nucleophiles is often influenced by subtle factors and both the N-hydroxymethyl or O-hydroxymethyl compounds are contemplated to be within the scope of the invention. Acylation of 12 (X=OH) affords esters 13 (R"=$(CH_2)_2$ $CO_2H$).

The acylation is conveniently carried out by contacting 12 (X=OH) with an acyl halide or acid anhydride in a solvent such as DCM, chloroform, carbon tetrachloride, ether, THF, dioxane, benzene, toluene, MeCN or DMF, optionally in the presence of an inorganic or organic base (e.g., triethylamine, DIPEA, DMAP or pyridine) at temperatures between –20 and 200° C., but preferably at temperatures between –10 and 80° C. to afford 6 (Y=alkyl or heteroaryl). The acylation may also be carried out with the free acid in the presence of an acid-activating agent or a dehydrating agent, e.g. isobutyl chloroformate, TMS-Cl, DCC, DCC/N-hydroxysuccinimide or HOBT, CDI, O-(benzotriazol-1-yl)-N,N,N',N'-tetramethyluronium tetrafluoroborate/NMM, O-(benzotriazol-1-yl)-N,N,N',N'-tetramethyl-uronium tetrafluoroborate/DIPEA, N,N'-thionyldiimidazole or $(C_6H_5)_3P/CCl_4$, at temperatures between –20 and 200° C., but preferably at temperatures between –10 and 80° C. (J. March, *Advanced Organic Chemistry* John Wiley & Sons, New York 1992 392-398; J. Mulzer *Synthesis of Esters, Activated Esters & Lactones in Comprehensive Organic Synthesis*, E. Winterfeldt, ed., vol. 6, Pergamon Press, Oxford 1991, pp. 324-340)

The 2,4-dihydro-[1,2,4]triazol-3-ones 16 used to prepare compounds of the present invention were prepared by cyclization of an N'-acyl-N-carbamoylhydrazide derivative according to formula 15. The requisite hydrazides are prepared by contacting an acylhydrazone 14b with an alkylisocyanate. Alternatively substituted phenylacetic acids 14c are condensed with a 4-alkyl-semicarbazide in the presence of a carboxylic acid activating group. Protocols for efficient activation and coupling of carboxylic acids with amine compounds have been extensively refined and optimized (see e.g., M. Bodanszky, *Principles of Peptide Synthesis*, Springer Verlag, New York 1993; P. Lloyd-Williams and F. Albericio *Chemical Methods for the Synthesis of Peptides and Proteins* CRC Press, Boca Raton, Fla. 1997). The N'-acyl-N-carbamoylhydrazides 15 were cyclized to a triazolone 16 by treatment with methanolic KOH or potassium tert-butoxide in tert-butanol.

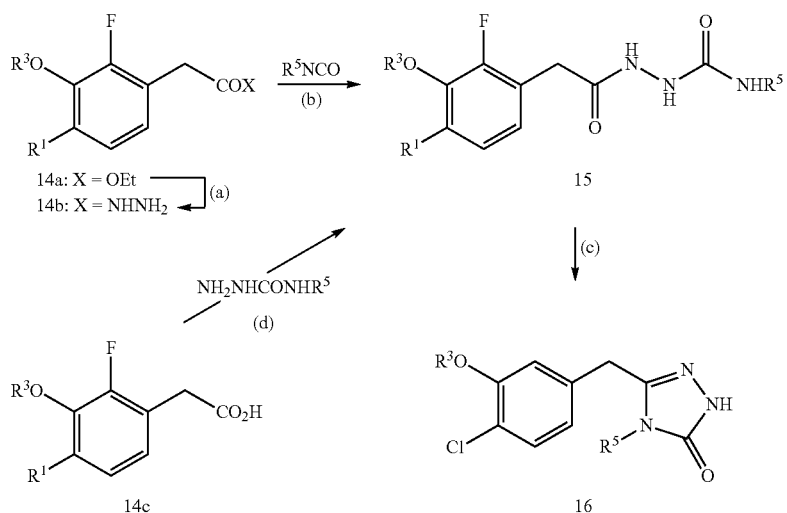

(a) NH$_2$NH$_2$, EtOH; (b) R$^5$NCO, THF; (c) KOH, MeOH or potassium tert-butoxide; (d) DCC 3-Phenoxy-phenyl-acetic acid compounds 14a and 14c which are useful intermediates for the synthesis of the present compounds have been described (J. Dunn, et al. U.S. Publication 20040192704, U.S. Publication 20040198736 and U.S. Non-Provisional Application filed Mar. 22, 2005). These applications are hereby incorporated by reference in their entirety.

Compounds of the present invention contain biaryl ethers and the preparation of diaryl ethers has been reviewed (J. S. Sawyer, *Recent Advances in Diaryl Ether Synthesis, Tetrahedron* 2000 56:5045-5065). Introduction of the aryloxy ether can often be accomplished by direct S$_N$Ar displacement on an aromatic ring substituted with a leaving group and electronegative substituents. Fluoroaromatic compounds with electronegative substituents are known to be sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides undergo facile displacement reactions even at room temperature (D. Boger et al., *Biorg. Med. Chem. Lett.* 2000 10: 1471-75; F. Ferrier *Nucleophilic Aromatic Displacement: The Influence of the Nitro Group* VCH Publishers, New York, N.Y. 1991). Phenols typified by 18a and 28a can be treated with appropriately substituted aryl fluorine compounds to produce diaryl ethers (infra).

Aryl ethers also can be efficiently prepared by Cu(OAc)$_2$ catalyzed condensation of substituted benzene boronic acids and phenols (D. A. Evans et al., *Tetrahedron Lett.*, 1998 39:2937-2940 and D. M. T. Chan et al., *Tetrahedron Lett.* 1998 39:2933-2936). This protocol can also be adapted to phenols such as 18a and appropriately substituted benzene boronic acids are widely available.

Alternatively, variations of the Ullmann diaryl ether synthesis with Cu(I) salts (J.-F. Marcoux et al., *J. Am. Chem. Soc.* 1997 119:10539-540; E. Buck et al, *Org. Lett.* 2002 4(9): 1623-1626) or palladium-catalyzed coupling procedures also has been reported (G. Mann et al., *J. Am. Chem. Soc.*, 1999 121:3224-3225) have been described. One skilled in the art will appreciate that optimal procedure will vary depending on the nature and position of substituents on the aryl rings to be coupled and useful conditions for the coupling can by identified without undue experimentation.

4-Chloro-2-fluoro-3-phenoxy-phenylacetic acid compounds (SCHEME 3) can prepared by starting from 1-chloro-3-fluoro-2-methoxy-4-methylbenzene (17a) utilizing a sequence (17a-17c) comprising benzylic bromination with NBS and AIBN, cyanide displacement, hydrolysis of the nitrile and esterification of the carboxylic acid. Demethylation of the ether affords a phenol 18a which can be used to introduce the biaryl ether by S$_N$Ar displacement of a fluorine substituent on a suitably substituted benzene (e.g., 5 fluoroisophthalonitrile) or by coupling with a substituted benzeneboronic acid under Suzuki conditions.

SCHEME 3

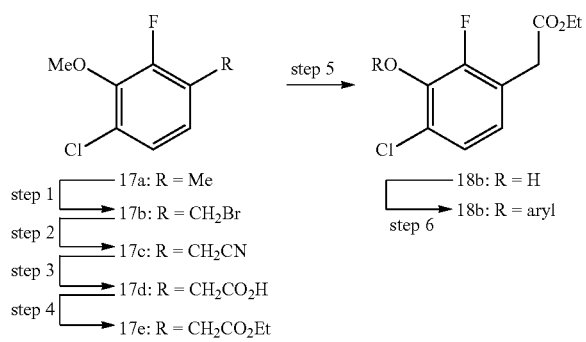

The synthesis of 2-fluoro substituted compounds also was accomplished starting from 1,2,3-trifluoro-4-nitro-benzene (19). Treatment of 19 with an alkali metal phenolate results in displacement of the 3-fluoro group with good regioselectivity to afford 20a (SCHEME 4). Treatment of 20a with carbanion formed by deprotonation of tert-butyl ethyl malonate results in the regioselective introduction of a malonic ester (20b) which is subjected to acid-catalyzed hydrolysis of the tert-butyl ester and decarboxylation to afford 20c. After introduction of the phenoxy and acetic acid moieties, the nitro group can be converted to other substituents at the 4-position. Reduction of the nitro substituent afforded 21a which was subjected to Sandmeyer conditions to introduce a bromo 21b or chloro 21e substituent. The bromo substituent was further reacted with a dialkyl zinc (the Negishi Reaction) to afford 4-alkyl-3-aryloxy-2-fluoro-phenylacetic acid compounds exemplified by 21c and 21d.

SCHEME 4

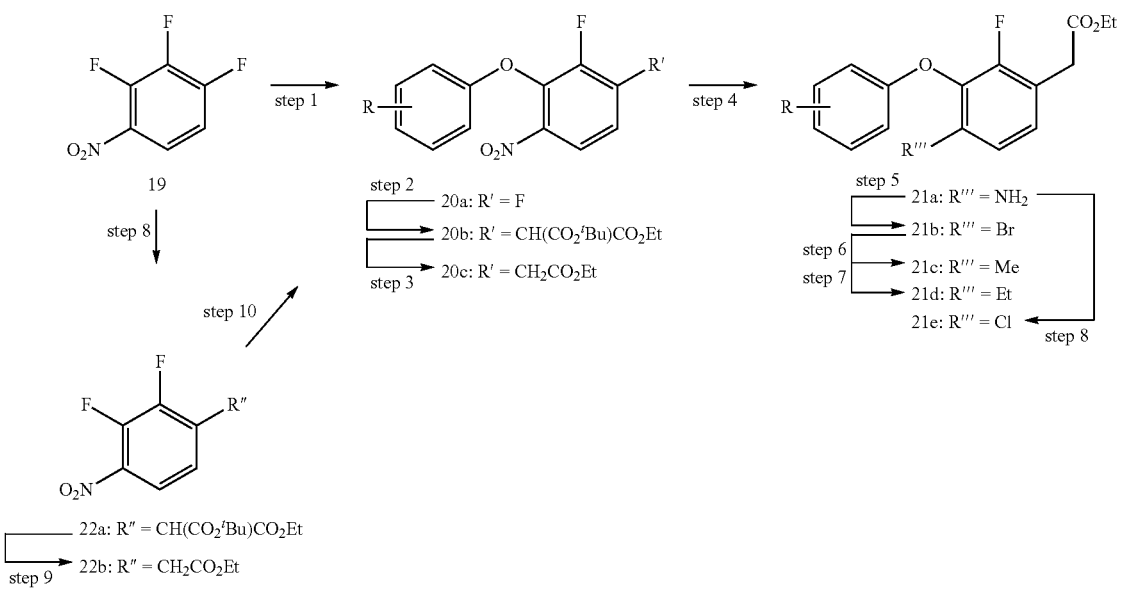

Alternatively, the reaction of the mixed tert-butyl ethyl ester of malonic acid affords a regioisomeric mixture of adducts in which displacement of the fluorine at the 1-position 22a predominates. The ratio of 1:3 isomers is approximately 2:1 and the isomers are conveniently separated by silica chromatography. Hydrolysis and decarboxylation of 22a affords the phenylacetic acid 22b which is an effective substrate for introduction of the aryl ether by a second $S_NAr$ displacement and replacement of the nitro group by Sandmeyer-type chemistry.

4-Alkoxy-2-fluoro-3-phenoxyphenylacetic acid compounds were prepared from o-difluorobenzene (SCHEME 5). A mixture ortho-difluorobenzene (23a) and trimethylsilylchloride was treated with butyl lithium to produce 2,3-difluoro-1,4-bis-trimethylsilanyl-benzene (23b) which was brominated to afford 23c. Selective monometallation of 23c with iso-propylmagnesium chloride-lithium chloride complex and quenching the organomagnesium compound with DMF afforded 23d. Reaction of 23d with a phenol in the presence of $K_2CO_3$ resulted in displacement of the fluorine atom adjacent to the aldehyde to afford 24a. The aldehyde was subjected to a Baeyer-Villiger oxidation with trifluoroperacetic acid which underwent concomitant hydrolysis to the phenol 24b which was alkylated with $Cs_2CO_3$ and methyl iodide to afford the methoxy substituted analog 24c. Metallation of the remaining bromine substituent with iso-PrMgCl/LiI/THF and allylation of the resulting Grignard reagent afforded 25a which was oxidatively cleaved with $NaIO_4$/Ru(III)$Cl_3$ to produce the phenylacetic acid 25b.

SCHEME 5

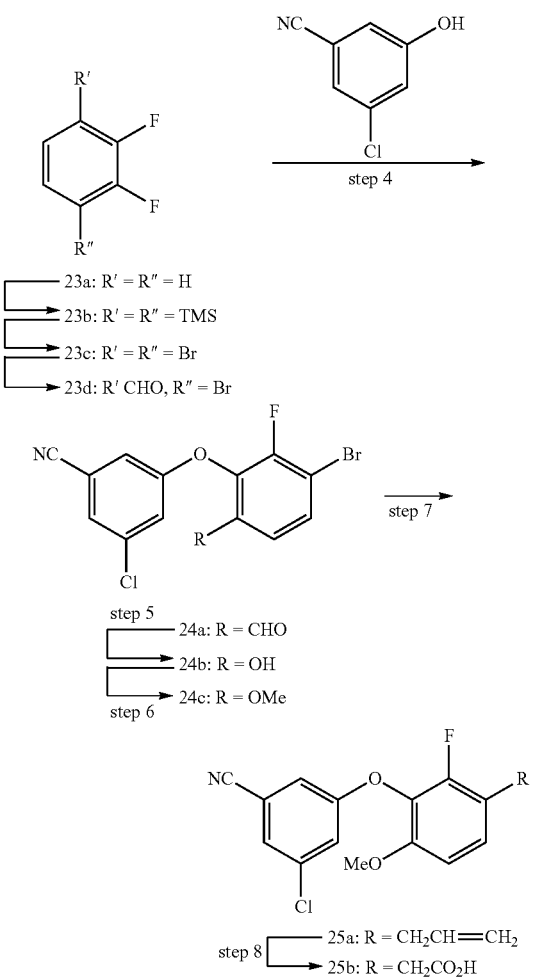

The substituted phenylacetic acid esters thus obtained were converted to the corresponding triazolones as described previously.

Useful aryl fluorides, such as 3-chloro-5-fluoro-benzonitrile, 1-bromo-3-chloro-5-fluoro-benzene, 5-fluoro-isophthalonitrile and 3,5-dibromo-fluoro-benzene are commercially available or readily prepared from commercially available precursors. 3-Difluoromethyl-5-fluoro-benzonitrile (34) was prepared by monometallation of 1,3-dibromo-5-fluorobenzene (33a) and quenching the aryl lithium intermediate with DMF and fluorinating the resulting benzaldehyde (33b) with DAST to afford 33c. Cyanide substituents can be introduced into a aromatic ring by $Zn(CN)_2$/palladium-catalyzed displacement of a halogen by cyanide which can be carried out either after formation of the biaryl ether or on a halogenated precursor (SCHEME 6) prior to formation of the ether. Displacement of the bromine substituent with zinc cyanide affords 34. These fluorinated compounds are suited to condensation with a phenolic substituent on the phenylacetic acid fragment. Phenols useful for condensation with 19 or 22b are also readily available. 3-Bromo-5-difluoromethyl-phenol (28b) can be prepared by fluorination of 3-acetoxy-5-bromo-benzaldehyde (27b) with DAST. Optionally, displacement of the bromine substituents by cyanide can be carried out either before or after formation of the biaryl ether. Thus treatment of 29 with $Zn(CN)_2$ and $Pd(Ph_3P)_4(0)$ affords 30. 3,5-dibromophenol is commercially available and palladium-catalyzed displacement of both bromine atoms by cyanide affords 5-hydroxy-isophthalonitrile. 3-Chloro-5-hydroxy-benzonitrile (31c) was prepared from 3,5-dichlorobenzonitrile by $S_NAr$ displacement with sodium methoxide and cleavage of the resulting methyl ether 31b. Condensation of 31c with 19 introduces the 3-chloro-5-cyano-phenoxy substituents into the phenylacetic acid containing a 4-nitro substituents for further modification of the 4-position. Similarly 3-bromo-5-chloro-phenol can be condensed with 22b and which was further converted to 32c.

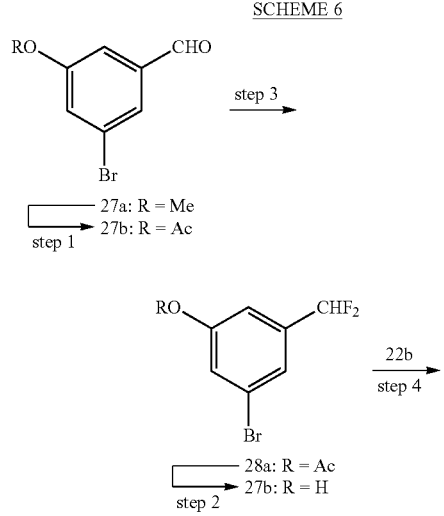

SCHEME 6

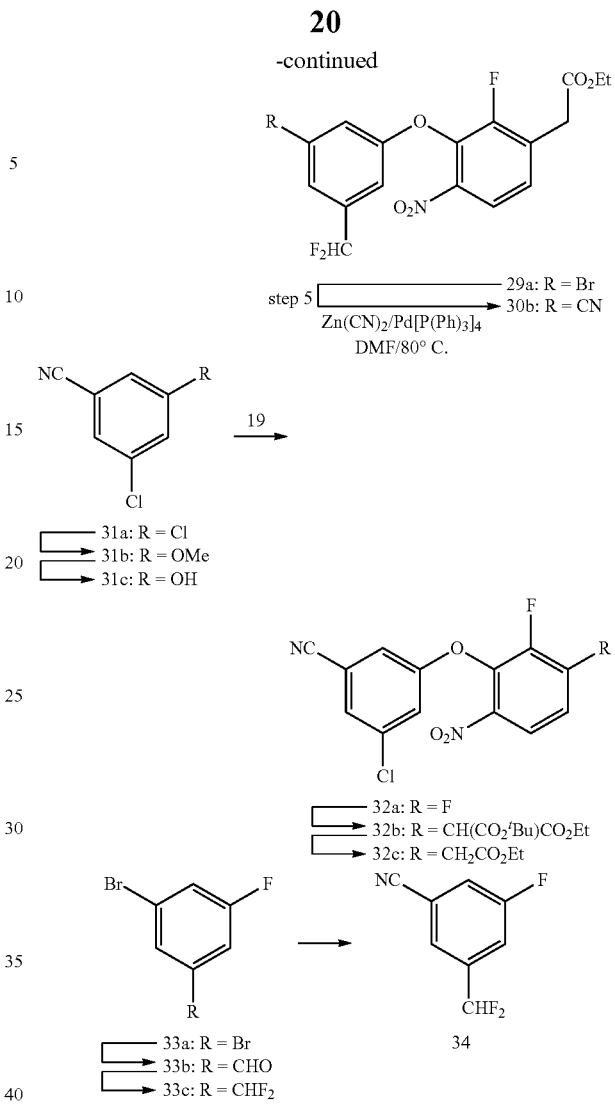

DOSAGE AND ADMINISTRATION

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable" as used herein means that which is useful in preparing a pharmaceutical composition that is generally safe, non-toxic, and neither biologically nor otherwise for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the viral load, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Example 1

Succinic acid mono-{3-[3-(3-cyano-5-difluorom-
ethyl-phenoxy)-2-fluoro-4-methyl-benzyl]-4-methyl-
5-oxo-4,5-dihydro-[1,2,4]triazol-1-ylmethyl}ester

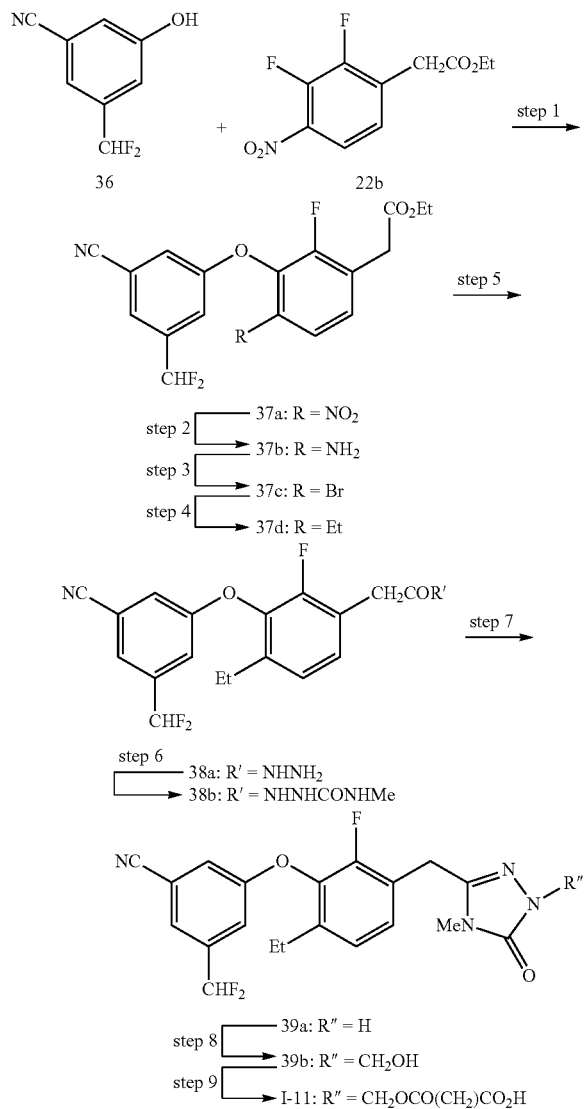

step 1—An oven-dried round bottom flask was charged with 36 (9.07 g, 54 mmol) and dry THF (90 mL). The solution was cooled to 0° C. under nitrogen and sodium tert-butoxide (5.27 g, 55 mmol) was added slowly over several minutes. The clear yellow solution was stirred for 10 minutes at 0° C. A separate oven-dried round bottom flask was charged with 22b (13.148 g, 54 mmol) under nitrogen and dry THF (90 mL) was added. This solution was added to the sodium phenolate solution maintained at 0° C. slowly via syringe over 10 min. After stirring at RT overnight, the reaction was slowly poured into cold, saturated aqueous $KHSO_4$ (100 mL) and extracted twice with EtOAc (2×200 mL). The organic layers were combined and washed with brine (100 mL). The solution was dried ($MgSO_4$), filtered and concentrated in vacuo. The crude product was recrystallized by dissolving in hot $Et_2O$ (100 mL), adding hexane (50 mL) and storing in refrigerator for several hours. The precipitate was filtered to afford 13 g of brown solid. The filtrate was concentrated and purified by $SiO_2$ column chromatography eluting with EtOAc/hexanes to afford 10 g of 37a as a yellow solid. The product was combined with precipitate and the mixture recrystallized under similar conditions as described above to obtain 20 g (94%) of 37a as white solid.

step 2—The bis-aryl ether 37a (16.36 g, 41.5 mmol), iron (9.732 g, 174 mmol), and $NH_4Cl$ (9.322 g, 174 mmol) were combined in a round bottom and suspended in EtOH (70 mL) and water (70 mL). The suspension was heated to reflux for 2.5 hrs, cooled to RT and filtered through CELITE®. The CELITE cake was washed repeatedly with EtOAc. The filtrate was combined and washed with brine, dried ($MgSO_4$), filtered and concentrated in vacuo. The crude material was purified by $SiO_2$ chromatography eluting with EtOAc/hexanes to afford 14.2 g (93%) of 37b as a white solid.

step 3—A 500 mL round bottom was charged the Cu(II) $Br_2$ (2.62 g, 11.7 mmol) and LiBr (3.052 g, 35.2 mmol). The mixture was purged with dry argon for 20 min. To this was added MeCN (150 mL) and stirred for 20 min at 50° C. until the solid particles were finely dispersed. To the suspension was added the tert-butyl nitrite and stirred continued for 5 min after which a solution of 37b (4.27 g, 11.72 mmol) and MeCN (40 mL) was added in a single portion. The resulting mixture was stirred at 70° C. for 1 h. The reaction mixture was cooled to 0° C. and quenched with 5% aqueous HBr (10 mL). The solution was diluted with EtOAc (200 mL) and washed with water (100 mL) and brine (50 mL). The organic layer was dried ($MgSO_4$), filtered and concentrated in vacuo. The crude material was purified by $SiO_2$ chromatography eluting with EtOAc/hexanes to obtain 2.6 g (52%) of 37c as a white solid.

step 4—An oven-dried round bottom flask was charged with the bromide 37c (3.0 g, 7 mmol) and Pd(dppf) $CH_2Cl_2$ (572 mg, 0.7 mmol). The mixture was purged with argon for 15 min. To the solid was added dry THF (35 mL), dimethylaminoethanol (0.14 mL, 1.4 mmol), and diethyl zinc (1.1 M in toluene, 12.7 mL, 14 mmol). The resulting mixture was warmed to 65° C. for 10 min then cooled to 50° C. After 1 h, the reaction mixture was cooled to RT and added to saturated aqueous $NH_4Cl$ (100 mL). The mixture was extracted with EtOAc (150 mL) and the organic layer was then washed with water (100 mL) and brine (50 mL). The organic layer was dried ($MgSO_4$), filtered and concentrated in vacuo. The crude product was purified by $SiO_2$ column chromatography eluting with EtOAc/hexanes to afford 2.3 g (90%) of 37d as a white solid.

step 5—To a 100 mL round bottom was charged with 37d (3.3 g, 8.75 mmol) and EtOH (25 mL). To this was added anhydrous hydrazine (4.12 mL, 131 mmol) and the resulting solution was heated to reflux for 2 h. The solution was cooled to RT and purified by $SiO_2$ chromatography eluting with MeOH/DCM. The product was recrystallized from warm EtOH to afford 3.0 g (94%) of 38a as a white solid.

step 6—To a 250 mL round bottom containing a solution of 38a (3.0 g, 8.26 mmol) and anhydrous THF (40 mL) under a nitrogen atmosphere was added methyl isocyanate (7.26 mL, 12.9 mmol) in a single portion. The resulting solution was stirred at RT for 4 h and concentrated to afford 3.45 g of 38b (99%) as a light yellow solid that was used without any further purification.

step 7—A round bottom flask was charged with 38b (3.4 g, 8 mmol) and tert-butanol (80 mL) under a nitrogen atmosphere. To this solution was added potassium tert-butoxide (91 mg, 0.8 mmol) and the mixture was heated to reflux under nitrogen. Additional potassium tert-butoxide was added after 24, 36 and 48 h (46 mg each addition, 0.4 mmol). After stirring for 60 h, the reaction was allowed to cool to RT and diluted with EtOAc (150 mL). The organic phase was washed with water (100 mL) and brine (50 mL), dried (MgSO$_4$), filtered and concentrated in vacuo. The crude material was then purified by SiO$_2$ chromatography eluting with MeOH/DCM to afford a solid which was recrystallized from warm EtOAc (50 mL) and hexanes (50 mL) to afford 1.85 g (56%) of 39a as a white solid (56%).

step 8—To a 100 mL round bottom flask charged with triazolinone 39a (1.75 g, 4.3 mmol) and MeOH (20 mL) was added in a single portion formaldehyde (37% in water, 14.1 mL, 174 mmol). The reaction was heated to reflux at 90° C. for 1 h, cooled and concentrated in vacuo to remove the MeOH. The product was extracted twice with DCM (2×100 mL). The organic layers were combined, dried (MgSO$_4$), filtered and concentrated in vacuo. The crude material was then purified by SiO$_2$ chromatography eluting with MeOH/DCM. The recovered product was subsequently recrystallized from warm EtOAc (30 mL) and hexanes (30 mL) to afford 1.85 g (98%) of 39b as a white solid.

step 9—A 100 mL round bottom flask was charged with triazolinone 39b (1.85 g, 4.3 mmol), DMAP (26 mg, 0.21 mmol), and succinic anhydride (471 mg, 4.70 mmol). To this was added DCM (25 mL) and DIPEA (0.82 mL, 4.70 mmol). The reaction was stirred at RT for 2 h. The reaction was then poured into a saturated aqueous NH$_4$Cl (50 mL) and extracted twice washed with dichloromethane (75 mL each). The organic layers were combined, dried (MgSO$_4$), filtered and concentrated in vacuo. The crude product was recrystallized from hot EtOH (50 mL) to afford 2.07 g (91%) of I-11a white solid (91%).

Example 2

Succinic acid mono-{3-[3-(3-cyano-5-difluoromethyl-phenoxy)-2-fluoro-4-methyl-benzyl]-4-methyl-5-oxo-4,5-dihydro-[1,2,4]triazol-1-ylmethyl}ester (I-7)

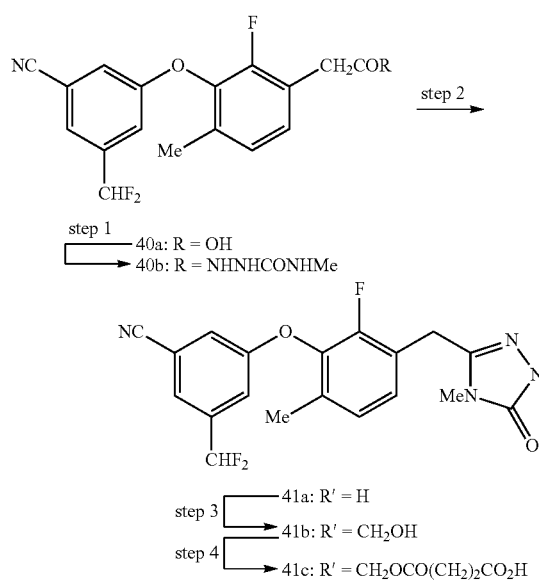

[3-(3-Cyano-5-difluoromethyl-phenoxy)-2-fluoro-4-methyl-phenyl]-acetic acid ethyl ester (40, R=OEt) was prepared as described in Example 1 except in step 4, Et$_2$Zn was replaced with Me$_2$Zn. The ethyl ester was hydrolyzed with LiOH and EtOH to afford 40a.

step 1—An oven-dried 100 mL round bottom flask maintained under N$_2$ was charged with 40a (1.14 g, 3.4 mmol), methyl semicarbazide (318 mg, 3.57 mmol) and MeCN (65 mL). A solution of DCC and anhydrous MeCN (20 mL) was added and the solution stirred overnight. The following day additional methyl semicarbazide (40 mg, 0.46 mmol) and DCC (105 mg, 0.46 mmol) was added. After an additional 3 h the reaction was filtered and concentrated in vacuo. The crude product was purified by SiO$_2$ chromatography eluting with MeOH/DCM to afford 1.0 g (76%) of 40b as a white solid.

step 2—To a solution of 40b (2.0 g, 4.9 mmol) and tert-butanol (49 mL) under a nitrogen atmosphere was added potassium tert-butoxide (55 mg, 0.49 mmol) and the mixture was heated to reflux under nitrogen. Additional potassium tert-butoxide (55 mg, 0.49 mmol) was added after 24 h. After stirring for 48 h, the reaction was cooled to RT and diluted with EtOAc (150 mL). The solution was washed with water (100 mL) and brine (50 mL). The organic layer was dried (MgSO$_4$), filtered and concentrated in vacuo. The crude product was recrystallized from EtOAc (50 mL) and hexanes (50 mL) to yield 1.60 g (84%) of 41a as a white solid.

step 3—To a solution of 41a (1.68 g, 4.3 mmol) and MeOH (86 mL) was added CH$_2$O (37% in water, 2.6 mL, 87 mmol) in a single portion. The reaction was heated to reflux for 11 h and the reaction was concentrated in vacuo to remove the methanol. The crude alcohol was recrystallized from H$_2$O (50 mL) to afford 1.45 g (77%) of 41b as a white solid.

step 4—A flask was charged with 41b (1.358 g, 3.25 mmol), DMAP (20 mg, 0.16 mmol), and succinic anhydride (357 mg, 3.57 mmol) and DCM (31 mL) and DIPEA (0.622 mL, 3.57 mmol) were added. The reaction was stirred at RT for 2 h. The reaction was then poured into 1 M aqueous HCl (50 mL) and extracted with DCM (2×75 mL). The organic extracts were combined, dried (MgSO$_4$), filtered and concentrated in vacuo. The crude product was purified by column SiO$_2$ chromatography (HOAc/EtOAc/hexanes) to afford 1.30 g (77%) of I-7 as white solid.

Example 3

Succinic acid mono-{3-[4-chloro-3-(3-chloro-5-cyano-phenoxy)-2-fluoro-benzyl]-4-methyl-5-oxo-4,5-dihydro-[1,2,4]triazol-1-ylmethyl}ester (I-2)

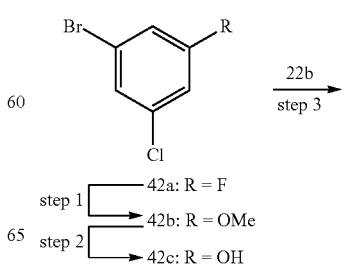

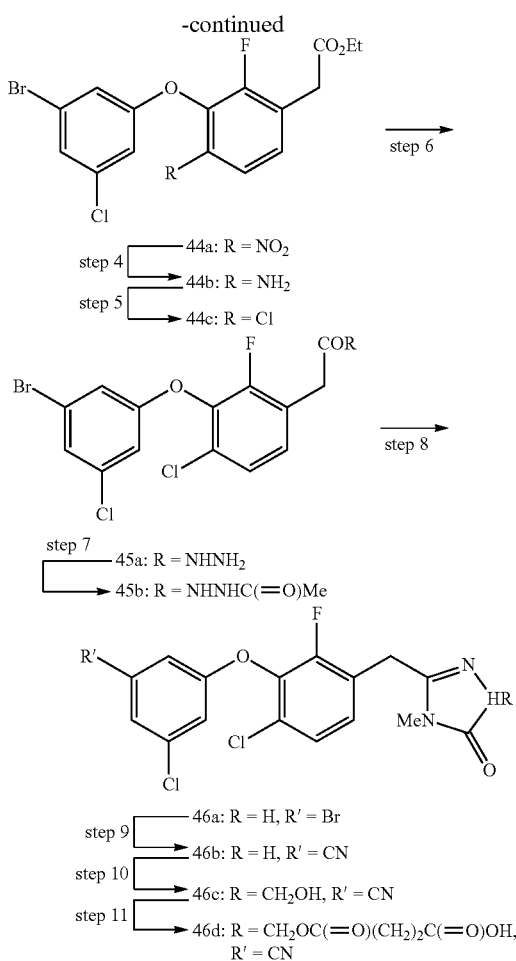

steps 1 and 2—A solution of 1-bromo-3-chloro-5-fluoro-benzene (42a, 55 g, 263 mmol) was cooled to 0° C. and treated with a 25% methanolic sodium methoxide solution (68 mL, 315 mmol) and heated to 40° C. for 3 h. The solution was cooled and partitioned between water (1 L) and a 1:1 mixture of hexane/diethyl ether (3×200 mL). The combined extracts were washed with brine (60 mL), dried ($Na_2SO_4$), filtered and the solvents evaporated in vacuo to afford 42b as an oil (57.3 g, 92% pure, 238 mmol). The ether 42b (43 g, 173 mmol) was treated with glacial HOAc (150 mL) and 48% aqueous HBr (100 mL) and heated to 120° C. After 40 h, the volatiles were removed while heated to 80° C. and then cooled to RT. The residue was partitioned between water (100 mL) and DCM (3×250 mL). The combined extracts were washed with $H_2O$ (50 mL), aqueous $NaHCO_3$ solution (2×50 mL), brine (50 mL), and ($MgSO_4$). The solvents were removed to afford 23.3 g of 42c as a grey solid.

step 3—To a solution of sodium tert-butoxide (4.2 g, 43.7 mmol) and THF (180 mL) maintained under an Ar atmosphere at RT was added a solution of 3-bromo-5-chloro-phenol (42c, 9.5 g, 45.7 mmol) and THF (35 mL). The resulting solution was aged at RT for 15 min. The solution was cooled to 0° C., and solution of 22b (10.2 g, 41.6 mmol) and THF (20 mL) was added over 3 min. The purple mixture was stirred at RT for 3 h, and then added to an aqueous solution of $NH_4Cl$ (150 mL) and extracted with $Et_2O$ (3×200 mL). The combined organic extracts were washed with 0.5 M aqueous NaOH (2×50 mL) and brine (100 mL), dried ($MgSO_4$), filtered and the volatiles were evaporated to afford 16.2 g of [3-(3-bromo-5-chloro-phenoxy)-2-fluoro-4-nitro-phenyl]-acetic acid ethyl ester (44a) as a tan solid.

steps 4 and 5—A suspension of 44a (16.1 g, 37 mmol), Fe powder (8.2 g, 148 mmol, Fisher, electrolytically deposited), and $NH_4Cl$ (8.0 g, 148 mmol) in absolute ethanol (700 mL) and $H_2O$ (180 mL) was heated to reflux for 4 h. The solution was cooled to RT and filtered through CELITE®. The filter cake was washed with chloroform (2×150 mL). The filtrate was washed with aqueous $NaHCO_3$, water, and brine and dried ($K_2CO_3$), filtered and the volatiles removed to afford 14.0 g of [4-amino-3-(3-bromo-5-chloro-phenoxy)-2-fluoro-phenyl]-acetic acid ethyl ester (44b). The aniline 44b (9.7 g, 24.1 mmol) was dissolved in anhydrous MeCN (100 mL) under nitrogen. This solution was added slowly to a mixture of tert-butyl-nitrite (7.1 mL, 60.3 mmol, assay 90%) and $CuCl_2$ (6.5 g, 48.2 mmol) that had been prepared under nitrogen and warmed to 50° C. The reaction temperature was maintained at 50° C. for 15 min, cooled to 0° C. and poured into 5% aqueous HCl solution (80 mL) and $Et_2O$ (150 mL). The mixture was extracted with EtOAc (3×150 mL), the combined extracts were washed with brine and dried ($MgSO_4$), filtered and the volatiles were removed. The residual oil was purified by flash $SiO_2$ chromatography eluting with EtOAc/hexanes (0% to 10% EtOAc) to afford 6.25 g of [4-chloro-3-(3-bromo-5-chloro-phenoxy)-2-fluoro-phenyl]-acetic acid ethyl ester (44c) as an oil.

step 6—To a solution of 44c (8.8 g, 20.8 mmol) and absolute EtOH (130 mL) was added hydrazine monohydrate (4.0 mL, 83 mmol) and the solution heated to reflux. After 7 h, the solution was cooled to RT and the volatiles were removed. The residue was dissolved in water (250 mL) and warm $CHCl_3$ (400 mL) and EtOAc (200 mL) and the organic extracts were dried ($Na_2SO_4$) filtered and evaporated to afford 8.3 g if 45a as an off-white powder.

steps 7 and 8—To a solution of 45a (8.3 g, 20.4 mmol) and THF (150 mL) at RT and was added methyl isocyanate (1.5 g, 26.4 mmol). After 5.5 h, the volatiles were removed which produced an unstirrable mass. The residue was resuspended in toluene (50 mL) and tetrahydrofuran (50 mL) and the volatiles removed again which afforded the semicarbazide 45b (9.5 g, 20.4 mmol) as an off-white powder. A suspension of 45b (1.9 g, 4.1 mmol) and MeOH (80 mL) was treated with sodium methoxide (0.5 M in MeOH, 18 mL, 9 mmol) and heated to reflux for 11 h, cooled and the volatiles were removed. The residue was partitioned between aqueous $NH_4Cl$ and $CHCl_3$ (4×100 mL) and the organic extracts were dried ($Na_2SO_4$), filtrated and evaporated. The crude product was filtered through a $SiO_2$ column eluting with a gradient (1:1 $CHCl_3$:EtOAc to 100% EtOAc to 5% EtOH/EtOAc) to afford 980 mg of 46a as a white powder.

step 9—A solution of 46a (2.32 g, 5.2 mmol) and DMF (60 mL) and subjected to vacuum-purge cycle three times with argon. The degassed solution was treated with $Zn(CN)_2$ (1.07 g, 9.1 mmol) and $(Ph_3P)_4P(0)$ (300 mg, 0.26 mmol) and resubjected to vacuum purge with argon while heating to 95° C. After 16 h, the volatiles were removed and the residue was partitioned between 10% $NH_4OH$ and $CHCl_3$ (3×150 mL). The combined organic extracts were dried ($Na_2SO_4$), filtered and evaporated in vacuo. The crude product was filtered through a $SiO_2$ column eluting with a gradient (1:1 $CHCl_3$/EtOAc to EtOAc to 5% EtOH/EtOAc) to afford 1.54 g of 46b as an off-white powder.

steps 10 and 11—A solution of 46b (1.7 g, 4.3 mmol), MeOH (90 mL) and 37% aqueous $CH_2O$ (18 mL) was heated at reflux. After 1.5 h, the solution was cooled under a stream of nitrogen. The reaction was concentrated and when the volume had been reduced to about 30 mL a solid precipitated and 10 g of ice was added. The solid was filtered and stored in vacuo at 50° C. overnight which afforded 1.81 g of 46c as a white powder. The hydroxymethyl adduct 46c (1.29 g, 3.05 g), succinic anhydride (320 mg, 3.2 mmol), DMAP (20 mg, 0.15 mmol), NMM (0.40 mL, 3.7 mmol) were dissolved in DCM (35 mL) and stirred at RT for 2.5 h. The mixture was poured into 0.5 M aqueous $KHSO_4$ and extracted with DCM. The combined extracts were dried ($Na_2SO_4$), filtered and evaporated to afford 1.3 g of crude product which was purified by filtration through a pad of $SiO_2$ eluting with a gradient (2:1 to 3:1 EtOAc/hexane then 3:1 EtOAc/hexane with 0.5% HOAc) to afford I-2: $^1$H NMR ($d_6$-DMSO, 300 MHz) δ 12.2 (br.s, 1 H), 7.82 (t, J=1.2 Hz, 1H), 7.54-7.46 (m, 3H), 7.34 (t, J=7.8 Hz, 1H), 5.63 (s, 2H), 4.10 (s, 2H), 3.14 (s, 3H) 2.52-2.43 (m, 4H), Anal. Calcd for $C_{22}H_{17}FCl_2N_4O_6$: C, 50.49; H, 3.27; N, 10.71. Found: C, 50.66; H, 3.34; N, 10.67.

Succinic acid mono-{3-[4-chloro-3-(3,5-dicyano-phenoxy)-2-fluoro-benzyl]-4-methyl-5-oxo-4,5-dihydro-[1,2,4]triazol-1-ylmethyl}ester was prepared in a similar manner except steps 1 and 2 were omitted and 3,5-dibromophenol was used in the place of 3-bromo-5-chlorophenol in step 3 to afford I-4: mp 141.6-143.3° C., MS (ES): m/z 512, $^1$H NMR ($d_6$-DMSO, 300 MHz) δ 12.2 (br.s, 1H), 8.23 (t, J=1.2 Hz, 1H), 7.95 (d, J=1.2 Hz, 2H), 7.52 (dd, J=1.5, 8.6 Hz, 1H), 7.35 (t, J=7.8 Hz, 1H), 7.34 (t, J=7.8 Hz, 1H), 5.63 (s, 2H), 4.09 (s, 2H), 3.14 (s, 3H) 2.52-2.43 (m, 4H), Anal. Calcd for $C_{23}H_{17}FClN_5O_6$: C, 53.76; H, 3.33; N, 13.63. Found: C, 53.68; H, 3.47; N, 13.35. 3,5-Dibromophenol was prepared from 3,5-dibromoanisole by demethylation with HBr/HOAc.

Example 4

Succinic acid mono-{3-[4-chloro-3-(3-cyano-5-difluoromethyl-phenoxy)-2-fluoro-benzyl]-4-methyl-5-oxo-4,5-dihydro-[1,2,4]triazol-1-ylmethyl}ester (I-5)

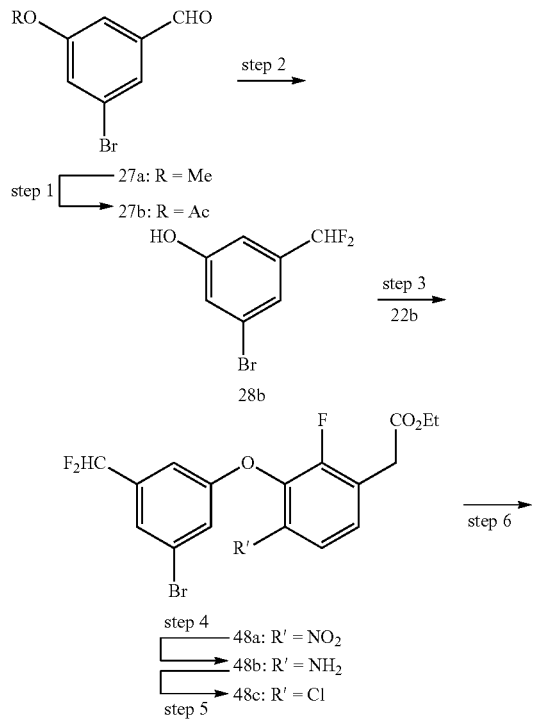

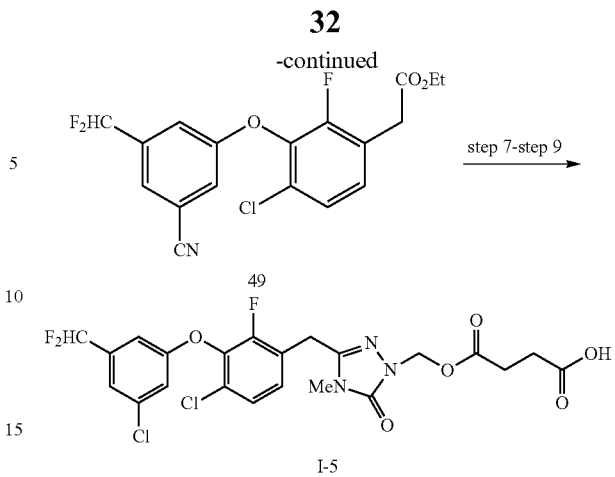

step 1—A solution of $BBr_3$ (29.1 mL of a 1.0 M solution in DCM, 29.1 mmol) was added slowly to a solution of 27a (2.5 g, 11.62 mmol) in anhydrous DCM (25 mL) maintained under $N_2$ at −78° C. The orange solution was warmed to RT, stirred for 2 h, and poured onto ice. The mixture was extracted with DCM (100 mL), and the organic layer was washed with $H_2O$ (50 mL) and brine (50 mL). The solvents were evaporated, and the remaining oil was purified by flash chromatography on silica gel eluting with a EtOAc/hexanes gradient (0% to 20% EtOAc) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (27b, 1.02 g, 40%).

step 2—DAST (1.02 mL, 7.69 mmol) was added to a solution of the 3-bromo-5-formyl-phenyl acetate (27b, 1.1 g, 4.52 mmol) in DCM (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated $NaHCO_3$. After the bubbling was finished, DCM (50 mL) was added and the layers were separated. The organic layer was washed with brine (30 mL) and dried with anhydrous $MgSO_4$. The solvent was removed to provide a yellow oil that was placed in a mixture of THF (15 mL) and $H_2O$ (4 mL). LiOH monohydrate (474 mg, 11.3 mmol) was added, and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried with anhydrous $MgSO_4$. Evaporation of the volatile materials gave an oil that was purified by flash chromatography on silica gel (0% to 25% EtOAc/hexanes) to provide 800 mg (79%) of 3-bromo-5-difluoromethylphenol (28b).

The phenol 28b was condensed with ethyl 2,3-difluoro-4-nitro-phenylacetate (22b) as described in step 3 of example 3. Reduction of the nitro group and diazotization and displacement of the diazonium salt by chloride (steps 4 and 5) were carried out as described in steps 4 and 5 of the previous example to afford 48c.

step 6—A flask was charged with 48c (28.6 g, 65 mmol), $Zn(CN)_2$ (4.60 g, 0.6 equiv), and $Pd[P(Ph)_3]_4(0)$ (7.5 g, 0.1 equiv) and maintained under Ar. DMF (200 mL) was added, and the mixture was heated to 80° C. for 4 h. The solution was cooled to 0° C. and filtered through a pad of $SiO_2$. The silica pad was washed with 300 mL of EtOAc and $NH_4OH$ (2N, 200 mL), $H_2O$ (100 mL), and hexanes (100 mL) were added to the mixture. The aqueous layer was separated and extracted with 600 mL of 1:1 EtOAc/hexanes. The combined organic extracts were washed with water and brine, dried (MgSO₄), filtered and concentrated in vacuo. The crude product was purified by SiO₂ chromatography eluting with a EtOAc/hexanes gradient (5 to 25% EtOAc) to afford 19.1 g (76%) of 49 as a white solid.

[4-Chloro-3-(3-cyano-5-difluoromethyl-phenoxy)-2-fluoro-phenyl]-acetic acid ethyl ester (49) was converted to the corresponding 4-methyl triazolone as described in steps 6-8 of Example 3. The triazolone was purified by SiO₂ chromatography eluting with MeOH/DCM gradient (1% to 3% MeOH) The hydroxymethylsuccinate was prepared by condensation with formaldehyde and subsequent acylation with succinic anhydride as described in steps 10 and 11 of Example 3 to afford I-5.

Example 5

Succinic acid mono-{3-[4-bromo-3-(3-cyano-5-difluoromethyl-phenoxy)-2-fluoro-benzyl]-4-methyl-5-oxo-4,5-dihydro-[1,2,4]triazol-1-ylmethyl}ester (I-9)

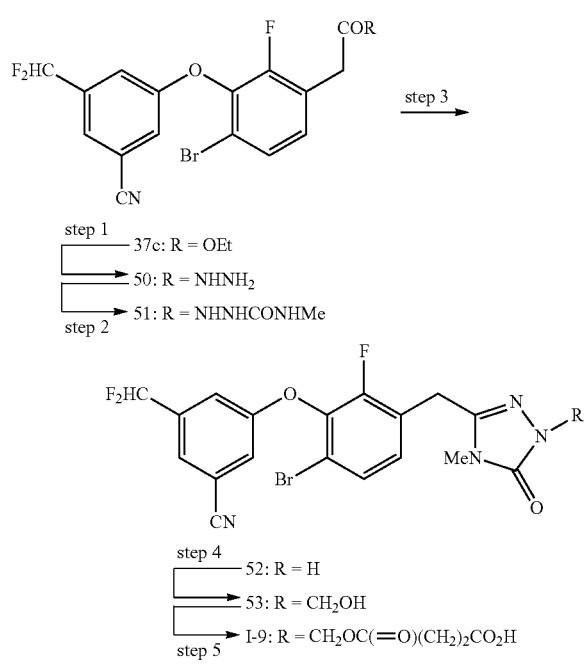

step 1—To a solution of 37c (2.71 g, 6.33 mmoles, from step 3 of Example 1) and absolute EtOH (25 mL) heated to reflux is added anhydrous hydrazine (1.99 mL, 63.3 mmoles) heating is continued for 2 h. The reaction was cooled and evaporated. The crude product was purified by SiO₂ chromatography eluting with EtOAc to afford 2.07 g (79%) of 50 as a white solid.

step 2—A suspension of 50 (12.15 g, 29.3 mmole) in dry THF (170 mL) was warmed until homogenous and then cooled to RT. To the resulting solution maintained under argon under argon is added slowly MeNCO (2.85 mL, 46.9 mmoles). The reaction mixture is stirred for 2 h and within 20 min a white precipitate appears. The reaction mixture was cooled to 0° C. and the white powder is filtered and washed with ether to afford 13.78 g (100% yield) of 51.

step 3—To a stirred solution of 51 (3.29 g, 6.98 mmoles) in warm HPLC grade tent-butanol (70 mL) of warm HPLC grade t-butanol is added potassium tert-butoxide (78 mg, 0.698 mmoles) and the mixture is heated to reflux under an argon atmosphere for 24 h. An additional aliquot of potassium tert-butoxide (40 mg) was added and heating continued for another 24 h. A third aliquot was added followed by heating for 24 h. The reaction mixture was cooled to RT and aqueous NH₄Cl (100 mL) was added. The mixture was twice extracted with EtOAc, the combined organic extracts washed twice with H₂O, dried (MgSO₄) and concentrated in vacuo. The crude product was purified by SiO₂ chromatography eluting with a MeOH/DCM gradient (3-5% MeOH). A minimum amount of EtOAc was added to the white solid recovered from the chromatography. This was sonicated, filtered and washed with a minimum quantity of EtOAc to afford 1.6 g (51%) of the triazolone 52.

step 4—A suspension of 52 (1.6 g, 3.53 mmoles), MeOH (35 mL), and 37% formaldehyde (28 mL) is heated at reflux for 3 h. The solution becomes homogeneous in about 15 min. The reaction mixture was cooled and concentrated in vacuo after which DCM (50 mL) was added with stirring. The organic phase was separated and the aqueous layer was extracted with DCM. The combined extracts were washed with H₂O, dried (MgSO4), filtered and concentrated in vacuo. The colorless oil (1.9 g) was purified by SiO₂ chromatography eluting with MeOH/DCM (2% to 4% MeOH). A minimum amount of DCM was added to the white foam and sonicated (a few drops of hexane was added until the solution was slightly turbid) which afforded 1.5 g (88%) of 53 as a white solid.

step 5—To a suspension of 53 (1.14 g, 2.36 mmoles), succinic anhydride (0.28 g, 2.83 mmoles), DMAP (14.4 mg, 0.118 mmoles) and DCM (10 mL) at RT under an Argon atmosphere was added DIPEA (0.54 mL, 3.06 mmoles) and reaction mixture was stirred 1 hr. To the clear solution was added 10% HCl (10 mL) and the aqueous phase twice extracted with DCM. The combined extracts were dried (MgSO4), filtered and concentrated in vacuo. A small amount of EtOAc was added to the white foam and the mixture sonicated, filtered, solid washed with 1:1 EtOAc/hexane and to afford 1.28 g (93%) of 1-9 as a white powder.

Example 6

Acetic acid 3-[4-chloro-3-(3-chloro-5-cyano-phenoxy)-2-fluoro-benzyl]-4-methyl-5-oxo-4,5-dihydro-[1,2,4]triazol-1-ylmethyl ester (I-12)

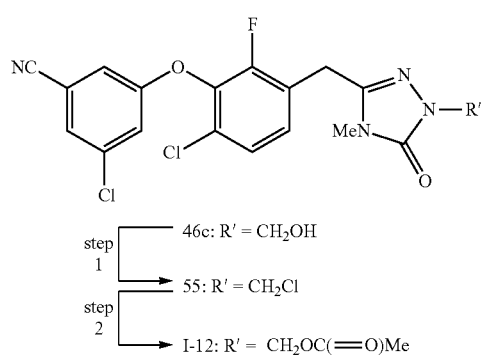

An oven-dried 100 mL round bottom was charged 46c (980 mg, 2.32 mmol, from step 10 of Example 3) and anhydrous DCM (20 mL) was added and the mixture maintained under a nitrogen atmosphere at −5° C. To the solution was added dropwise over several min SOCl$_2$ (177 mL, 2.43 mmol). The reaction was stirred at −5° C. under nitrogen for 1 h. The reaction was poured into brine (10 mL) and the resulting mixture was extracted with DCM (2×10 mL). The combined organic layers were dried (MgSO$_4$), filtered and concentrated in vacuo. The crude product was purified by SiO$_2$ chromatography eluting with EtOAc/hexanes) to afford 825 mg (81%) of 55 as a white foam.

An oven dried round bottom flask was charged with 55 (180 mg, 0.41 mmol) maintained under a stream of nitrogen. To this was added silver oxide (142 mg, 0.61 mmol) and acetic acid (69 μL, 1.22 mmol). The mixture was stirred under an N$_2$ atmosphere at RT. After 3 h, the crude material was filtered through a pad of SiO$_2$ and washed with 10% MeOH/DCM (50 mL). The filtrate was concentrated and the crude product purified by SiO$_2$ chromatography eluting with 10% MeOH/DCM) to afford 120 mg of 1-12 as a white foam (63%).

Example 7

Succinic acid mono-{3-[3-(3-chloro-5-cyano-phenoxy)-2-fluoro-4-methoxy-benzyl]-4-methyl-5-oxo-4,5-dihydro-[1,2,4]triazol-1-ylmethyl}ester (56b)

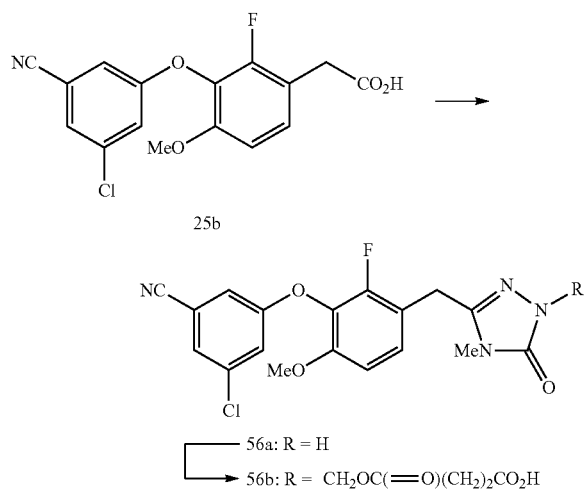

See SCHEME 5 for steps 1 to 8.

step 1—To a solution of di-iso-propylamine (150 mL, 108.3 g, 1.07 mol) in THF (500 mL) cooled to −78° C. and maintained under a N$_2$ atmosphere was added over 1 15 min period, n-BuLi (100 mL, 1.00 mol, 10M in hexanes). The resulting mixture was stirred for 30 min at −78° C. A mixture of 23a (45 mL, 52.110 g, 0.457 mol) and chlorotrimethylsilane (130.0 mL, 111.28 g, 1.024 mol) was added at a rate which maintained the internal reaction temperature below −50° C. The solution was stirred at −78° C. for 1 h. The reaction was quenched at −78° C. by addition of 1M H$_2$SO$_4$, diluted with MTBE and the mixture was saturated with solid NaCl. The phases were separated and the aqueous phase was extracted with MTBE (300 mL). The combined organic extracts were dried (MgSO$_4$), filtered and the solvents evaporated to afford 118 g (100%) of 23b as a white solid.

step 2—To neat bromine (76.9 mL, 1.50 mol) cooled to 0° C. in an ice bath was added portion wise solid 23b (126.23 g, 0.500 mol) while maintaining the internal temperature between 20-45° C. (caution: exothermic !). The reaction mixture was stirred at 58° C. for 2 h. After 1 h of this period had elapsed additional bromine (45.48 g) was added and the addition funnel was rinse with cyclohexane (10 mL). The reaction mixture was cooled to 0° C. and slowly poured into ice-cold saturated NaHSO$_3$ solution. After the addition the resulting mixture was saturated with solid NaCl, extracted with MTBE (500 mL and 200 mL), dried (MgSO$_4$) and concentrated in vacuo to afford 191 g of 23c. The reaction mixture was distilled at ca. 60 mbar which afforded 161.53 g of colorless liquid which boiled at 110° C. and contained about 11% of the monobromo derivative. The product was redistilled through a bubble ball column at ca. 50 mbar which afforded 141.3 (78.5%) of 23c with a boiling point of 93-94° C. which was >99.6 pure.

step 3—Preparation of iso-PrMgCl.LiCl—A sample of LiCl (4.56 g, 107.6 mmol) was dried under high vacuum with a heat gun for 10 min. To the dry solid under a N$_2$ atmosphere at 23° C. was added iso-PrMgCl (53.8 mL, 107.6 mmol, 2M solution in THF) and the resulting mixture was stirred at 23° C. for 3 days.

To a solution of 23c (1.29 mL, 10 mmol) in THF (5 mL) at −40° C. was added the iso-PrMgCl.LiCl solution (5.5 mL, 11 mmol, 2.0M in THF) at a rate that maintained the reaction temperature below −30° C. Stirring was continued at −35 to −30° C. for 1 h then warmed to −7° C. for an additional 1 h. The reaction mixture was cooled to −30° C. and DMF (1.00 mL, 13 mmol) was added in one portion (temperature rose to −23° C.) and stirring continued for 3.5 h at −25 to +15° C. The reaction mixture was poured into 1M H$_2$SO$_4$ and ice and the resulting mixture was saturated with solid NaCl and twice extracted with MTBE. The combined extracts were dried (MgSO$_4$), filtered and concentrated in vacuo to afford 2.17 g (98%) of 23d as a white solid.

step 4—To a solution of 3-chloro-5-hydroxy-benzonitrile (3.84 g), K$_2$CO$_3$ powder (4.2 g) and n-butyl nitrile was added 23d (5.57 g). The reaction mixture was heated to reflux for 4.5 h when the reaction appeared complete by gc/ms. The reaction mixture was cooled and poured into water and then EtOAc was added. The resulting mixture was allowed to stand until the layers separated. Some crystals were present at the interface and along the walls of the upper layer which were filtered and washed with water and hexanes. The filtrate was evaporated in vacuo, the residue taken up in IPA and re-evaporated. The solid was triturated with hexane and filtered. The mother liquor was evaporated and the residue purified by SiO$_2$ chromatography eluting with hexane/EtOAc (80:20). The product was triturated with IPA, filtered and washed with hexanes and the product fractions combined to afford 1.45 g (83%) of 24a.

step 5—Trifluoroacetic anhydride (8.88, 4.231 mmol) was added to a 100 mL round bottom and stirred at 0° C. 30% Hydrogen peroxide (0.290, 8.46 mmol) was then added dropwise to the reaction vessel and stirred for 2 hours at zero to produce trifluoroperacetic acid (TFPA).

To a solution of 24a (2.0, 5.64 mmol) in DCM (20 mL) stirred at 0° C. was added KH$_2$PO$_4$ (15.35 g, 112.82 mmol). To this suspension was added dropwise at 0° C. the TFPA. The reaction was stirred for 48 h. Upon consumption of starting material reaction mixture was cooled to 0° C., and diluted with brine, and quenched with aqueous 10% sodium bisulfite. The resulting mixture was extracted with DCM and washed with brine, dried (Na$_2$SO$_4$), filtered and the solvent removed in vacuo to yield a yellow solid which was purified by SiO$_2$ chromatography eluting with hexane/EtOAc (92:8) to afford 1.8 g (94%) of 24b.

step 6—To a solution of 24b (1.8 g, 5.26 mmol) in DMF (15 mL) was added Cs$_2$CO$_3$ (3.43, 10.52 mmol) and iodomethane (0.74 g, 5.26 mmol). The reaction mixture was stirred at 85° C. for 12 h. When 24b was consumed, the reaction mixture was cooled to RT and the cured mixture extracted with EtOAc and the combined extracts washed with water and brine. The EtOAc was dried (Na$_2$SO$_4$), filtered and concentrated in vacuo to afford 24c as a yellow oil which was used in the next step without additional purification.

step 7—A dry 100 mL round bottom was purged with nitrogen and charged with 24c (1.6 g, 4.50 mmol) and anhydrous THF (20 mL). The mixture was cooled to –20° C. and a solution of iso-PrMgCl.LiCl (5.40 ml, 5.40 mol, 2M in THF, see step 3) was added dropwise. The reaction was stirred for 2 h at –20° C. and a solution of CuCN LiCl (0.100 mL, 0.100 mol 1 M in THF) was added and stirred continued at –20 C. To this mixture was added allyl bromide (1.08 g, 9.0 mmol) and the mixture stirred for an additional two h. The reaction was quenched by addition of aqueous NH$_4$Cl. The mixture extracted with EtOAc and washed with water and brine. The extracts were dried (Na$_2$SO$_4$), filtered and the solvent was removed in vacuo to yield a yellow oil. The crude product was purified by SiO$_2$ chromatography eluting with hexane/EtOAc (95:5) to afford 1 g (70%) of 25a.

step 8—To a solution of 25a (0.100 g, 0.315 mmol), EtOAc (2 mL), MeCN (2 mL) and water (3 mL) was added NaIO$_4$ (0.437 g, 2.050 mmol) and RuCl$_3$ (0.001 g, 0.006 mmol). When 25a was consumed, the crude mixture was filtered through a pad of CELITE®, washed with EtOAc and the combined EtOAc washes were washed with brine, dried (Na$_2$SO$_4$) filtered and evaporated in vacuo to afford 0.090 g (85%) of 25b as a yellow solid. The ethyl acetate was dried over sodium sulfate and filtered. Solvent was removed in vacuo to yield 25b as a yellow solid (0.090 g, 85%).

The phenylacetic acid 25b was converted into the triazolone 56a by the procedure described in steps 1 and 2 of example 2. The triazolone will be converted to 56b by the procedure described in steps 8 and 9 of example 1.

Example 8

3-Difluoromethyl-5-hydroxy-benzonitrile (36)

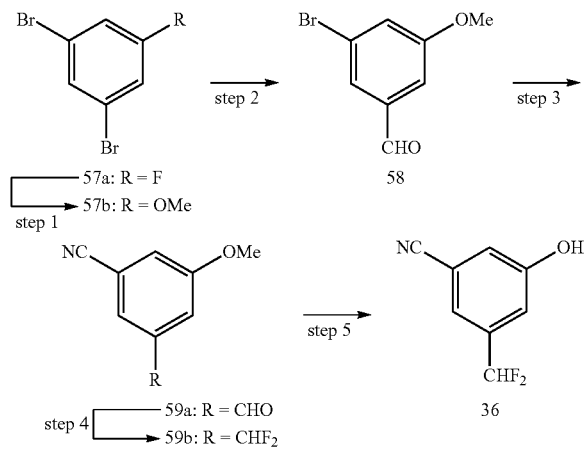

step 1—A solution of 57a, sodium methoxide (1 equivalent) and DMF were stirred overnight under an N$_2$ atmosphere at RT. The volatile solvents were removed in vacuo and the residue partitioned between Et$_2$O and water. The organic phase was washed with 5% NaOH, water and brine, dried (MgSO$_4$), filtered and evaporated to afford 57b.

step 2—To a solution of 57b (60 g, 0.2256 mol) and anhydrous Et$_2$O (1 L)cooled to –78° C. and maintained under an Ar atmosphere was added dropwise over 30 min n-BuLi (100 mL, 0.2482 mol, 2.5M in hexane). The yellow solution was stirred at –78° C. for 20 min. To the reaction mixture was added dropwise dry DMF (19 mL, 248.2 mmol) over 15 min and the reaction stirred at –78° C. for 10 min before the cooling bath was removed and the reaction allowed to warm to –30° C. over 30 min. The reaction vessel was placed in an ice-water bath and warmed to –10° C. The mixture was slowly added to an ice cold saturated aqueous NH$_4$Cl solution (400 mL). The organic layer was separated and the aqueous phase thrice extracted with Et$_2$O. The combined extracts were washed with water, dried (MgSO$_4$), filtered and evaporated to afford an oil which solidified on standing. The crude product was purified by SiO$_2$ chromatography eluting with a hexane/EtOAc gradient (97:3 to 95:5) to afford 58.

step 3—Cyanation of 58 to afford 59a was carried out with Zn(CN)$_2$, Pd(PPh$_3$)$_4$(0) and DMF as described in step 9 of example 3 step 4—DAST (21.04 mL, 519 mmol) was added to a solution of 59a (15.1 g, 94 mmol) in DCM (100 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO$_3$. After the bubbling was finished, DCM (50 mL) was added and the layers were separated. The organic layer was washed with brine (30 mL) and dried with anhydrous MgSO$_4$. The solvent was removed and the crude product was purified by two flash chromatographies on silica gel (0% to 10% EtOAc/hexanes) to 59b as a white solid.

step 5—The methyl ether 59b was demethylated with HBr and glacial HOAc as described in step 2 of example 3 to afford 36.

Example 9

Determination of Pharmacokinetic Parameters

Intact female rats weighing 200-250 g were used. Groups of three or five rats were used for each dose level of an experimental compound and one rat was used as a vehicle control. Animals were allowed normal access to chow and water throughout the experiment. The test substance was formulated as an aqueous suspension containing hydroxypropyl cellulose, polysorbate 80 and benzyl alcohol adjusted to pH 3.5 with HCl or NaOH at a dose equivalent to (0.127 mmol) and was administered orally by gavage. A blood sample (0.3 mL) was collected from the treated rats at, 2, 4, 6 and 8 h from the orbital sinus and at 24 h by cardiac puncture. A sample of at least 0.3 mL of blood was withdrawn from the untreated animals 3 h after dosing. Potassium oxalate/NaF and lithium heparin were added to the samples which were stored on ice during sampling procedure. The samples were spun in a refrigerated centrifuge at –4° C. as soon as possible and the plasma samples were stored –20° C. immediately after centrifugation and later transferred to a –80° C. freezer until analysis. Aliquots of plasma (0.05 mL) were mixed with 0.35 mL of an internal standard (and 0.05 mL of acetonitrile containing 0.1% formic acid. A set of calibration standards was prepared by mixing 0.05-mL aliquots of plasma from untreated rats with 0.05-mL aliquots of standard solution in acetonitrile containing 0.1% formic acid and 0.35-mL aliquots of the internal standard in acetonitrile containing 0.1% formic acid). Each plasma sample and calibration standard was vortexed thoroughly and then centrifuged (3000×g) at 4°

C. for 20 min to precipitate the protein. Each supernatant from centrifugation was transferred into a separate injection vial for LC/MS/MS analysis.

TABLE 2

| Compound | Dose (mg/kg) | AUC[1,4] (μg·h/mL) | Cp[2,4] (2 h) (μg/mL) | Cp[4] (6 h) (μg/mL) |
|---|---|---|---|---|
| I-5 | 200 | 182 | 10.7 | 13.4 |
| I-5 | 700 | 233 | 10.5 | 15.6 |
| parent[3] | 152 | 68.8 | 2.74 | 5.02 |
| parent | 530 | 85.4 | 3.18 | 5.97 |
| I-2 | 200 | 204 | 10.5 | 15.2 |
| I-2 | 700 | 218 | 11.4 | 13.9 |
| I-9 | 200 | 189 | 7.37 | 14.8 |
| I-9 | 700 | 272 | 9.4 | 20.5 |
| I-7 | 200 | 127 | 8.60 | 8.72 |
| I-7 | 700 | 214 | 12.1 | 12.9 |
| I-4 | 200 | 372 | 11.8 | 21.8 |
| I-4 | 700 | 613 | 13.3 | 27.5 |

[1] AUC = Area under a concentration vs. time (0-24 h) curve calculated by the linear trapezoid rule.
[2] Cp is plasma concentration at designated time following injection.
[3] Parent compound

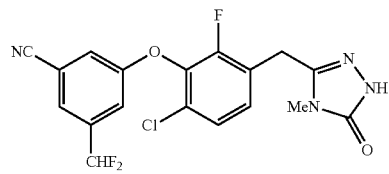

Doses for I-5 and the parent compound are equimolar.
[4] In all cases the compound measured in the plasma was the parent triazolone. Prodrug concentrations were at or below the detection level of the assay.

Example 8

Pharmaceutical Compositions

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A method for treating an HIV infection, or treating AIDS or ARC, comprising administering to a host in need thereof a therapeutically effective amount of a compound according to formula I wherein:

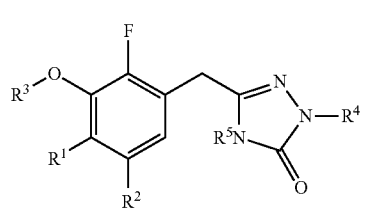

(I)

$R^1$ is halogen, $C_{1-6}$ alkyl or $C_{1-6}$ alkoxy;
$R^2$ is hydrogen, halogen or $C_{1-6}$ alkyl;

R³ is a phenyl substituted with one to three substituents independently selected from the group consisting of $C_{1-6}$ alkyl, $C_{3-8}$ cycloalkyl, $C_{1-6}$ haloalkyl, $C_{1-6}$ haloalkoxy, halogen, and cyano;

R⁴ is $CH_2OH$, $CH_2OC(=O)(CH_2)_2C(=O)OH$ or $CH_2OC(=O)C_{1-6}$ alkyl;

R⁵ is hydrogen or $C_{1-6}$ alkyl; or, a pharmaceutically acceptable salts thereof.

2. A method for treating HIV infection according to claim 1 further comprising co-administering at least one compound selected from the group consisting of HIV protease inhibitors, nucleoside reverse transcriptase inhibitors, non-nucleoside reverse transcriptase inhibitors, CD-4 binding ligands, CCR5 and CXCR4 inhibitors and viral fusion inhibitors.

3. A method according to claim 2 wherein the reverse transcriptase inhibitor is selected from the group consisting of zidovudine, lamivudine, didanosine, zalcitabine, stavudine, rescriptor, sustiva, viramune, efavirenz, nevirapine and delavirdine and/or the protease inhibitor is selected from the group consisting of saquinavir, ritonavir, nelfinavir, indinavir, amprenavir and lopinavir and/or a CD-4/CCR5/CXCR4/viral fusion inhibitor is selected from the group consisting of T-20, BMS-378806, BMS-488043; Sch-351125, Sch-350634, Sch-417690, UK 4278957, TAK-779, ONO-4128, AK-602, KRH-1636, T-22 and T-134.

4. A method for inhibiting HIV reverse transcriptase comprising administering a compound according to claim 1.

5. A method according to claim 4 wherein the host is infected with a strain of HIV expressing a reverse transcriptase with at least one mutation compared to wild type virus.

6. A method according to claim 5 wherein said strain of HIV exhibits reduced susceptibility to efavirenz, nevirapine or delavirdine.

* * * * *